(12) United States Patent
Bjornson et al.

(10) Patent No.: US 6,284,113 B1
(45) Date of Patent: Sep. 4, 2001

(54) APPARATUS AND METHOD FOR TRANSFERRING LIQUIDS

(75) Inventors: Torleif Ove Bjornson, Gilroy; Timothy F. Smith, Martinez, both of CA (US)

(73) Assignee: Aclara BioSciences, Inc., Hayward, CA (US)

( * ) Notice: Subject to any disclaimer, the term of this patent is extended or adjusted under 35 U.S.C. 154(b) by 0 days.

(21) Appl. No.: 09/153,814

(22) Filed: Sep. 15, 1998

Related U.S. Application Data

(60) Provisional application No. 60/059,333, filed on Sep. 19, 1997.

(51) Int. Cl.[7] .................. G01N 27/26; G01N 27/447; B01L 3/02; C12M 1/00; C12M 1/34
(52) U.S. Cl. .................. 204/453; 204/450; 204/451; 204/600; 204/601; 204/604; 422/100; 435/287.1; 435/287.2; 73/863.31; 73/863.32
(58) Field of Search .................. 422/100; 435/287.1, 435/287.2; 73/863.32, 863.31, 864, 864.01; 204/450, 451, 453, 600, 601, 604

(56) References Cited

U.S. PATENT DOCUMENTS

| | | | |
|---|---|---|---|
| 4,314,263 | 2/1982 | Carley | 347/48 |
| 4,383,265 | 5/1983 | Kobashi | 347/55 |
| 4,658,269 | * 4/1987 | Rezanka | 346/75 |
| 4,768,044 | 8/1988 | Shimosato | 347/55 |
| 4,799,068 | 1/1989 | Saito et al. | 347/55 |
| 4,948,564 | * 8/1990 | Root et al. | 422/102 |

FOREIGN PATENT DOCUMENTS

| | | |
|---|---|---|
| 60-46257 | 3/1985 | (JP) . |
| 9402381 | 10/1994 | (WO) . |

OTHER PUBLICATIONS

Dong Ho Chai, et al., Continuous Gray–scale Printing With the Electrohydrodynamic Ink–Jet Principle, *Eighth International Congress on Advances in Non–Impact Printing Technologies*, pp. 334–339 (1992). No month available.

I Hayati, et al., Investigations Into The Mechanisms of Electrohydrodynamic Spraying of Liquids, *Journal of Colloid and Interface Science*, 117/1, 205–221, (1987). No month available.

Ross N. Mills, Esijet™ Printing Technology, IS&T's NIP, 12, pp. 262–266. No date available.

(List continued on next page.)

*Primary Examiner*—Jill Warden
*Assistant Examiner*—John S. Starsiak, Jr.
(74) *Attorney, Agent, or Firm*—Larry W. Thrower; Iota Pi Law Group

(57) ABSTRACT

The present invention concerns devices, apparatus and methods for transferring liquids. One aspect of the present invention is a device comprising a plate having a plurality of transfer elements. Each of the transfer elements comprises an aperture in the plate where the aperture is capable of being electrically activated. The plate has one of more attaching elements for attaching the plate to a multiwell plate to form a sealed system except for the apertures of the transfer elements. Usually, the device is adapted for sealing attachment to a multiwell plate. In a method in accordance with the present invention a quantity of liquid is disposed to a second side of a plate having a plurality of apertures in the plate. The apertures are capable of being electrically activated. The liquid is present in a closed well except for the apertures in the plate. To simultaneously expel liquid from the apertures, the apertures are electrically activated. Also disclosed are kits comprising a device in accordance with the present invention.

35 Claims, 10 Drawing Sheets

OTHER PUBLICATIONS

I. Hayati, et al., Investigations into the Mechanism of Electrohydrodynamic Spraying of Liquids, *Journal of Colloid and Interface Science*, 117/1, pp. 222–230 (1987). No month available.

G. M. H. Meesters, Generation of Micron–Sized Droplets From the Taylor Cone, *J. Aerosol. Sci.*, 23/1, pp. 37–49 (1992). No month available.

G. H. Joffre et al., Characteristic Forms of Electrified Menisci Emitting Charges, *Journal of Electrostatics*, 18:147–161, (1986). No month available.

D. A. Saville, Electrohydrodynamics: The Taylor–Melcher Leaky Dielectric Model, *Annu. Rev. Fluid Mech.*, 29:27–64 (1997). No month available.

V. I. Kozhenkov et al., Electrohydrodynamic Atomisation of Liquids, *Russian Chemical Reviews*, 45/12, 1179–1184, (1976). No month available.

* cited by examiner

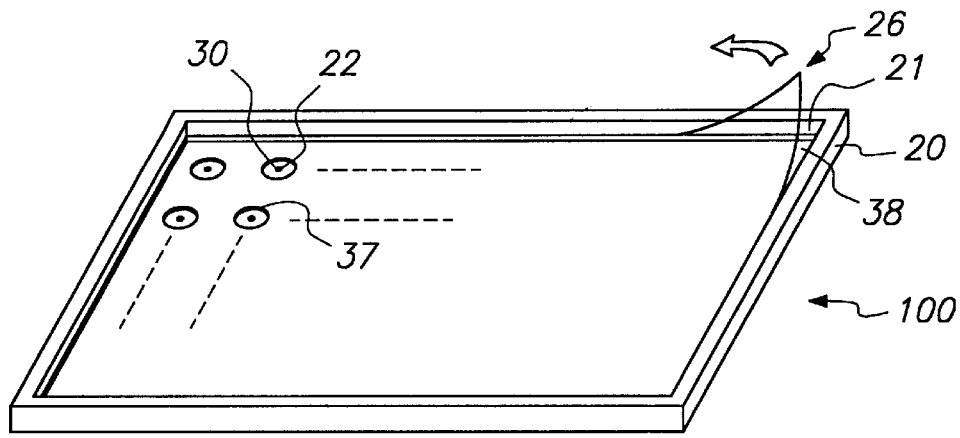
FIG. 1
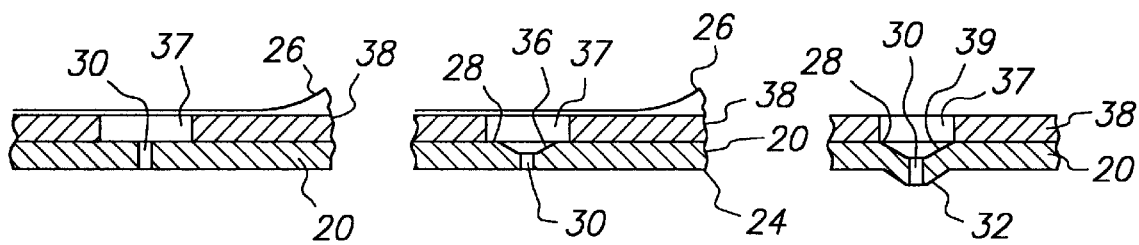
FIG. 2A  FIG. 2B  FIG. 2C
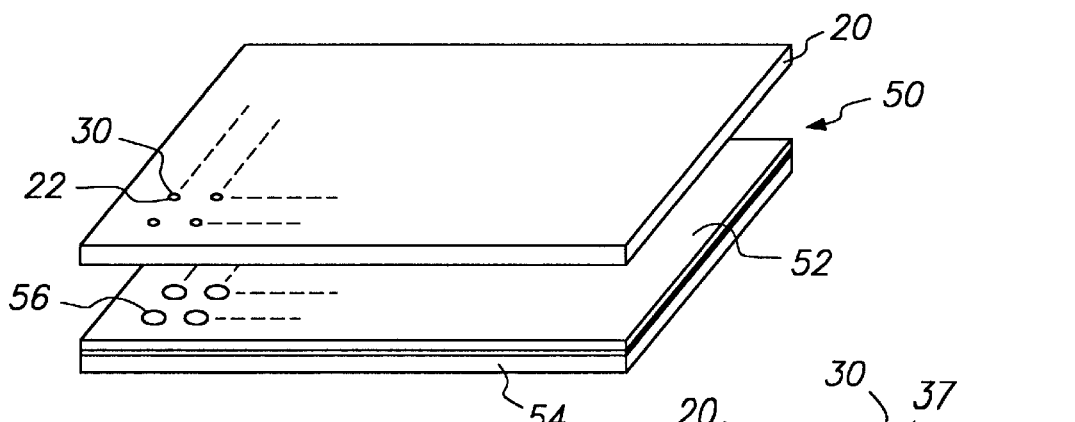
FIG. 3A
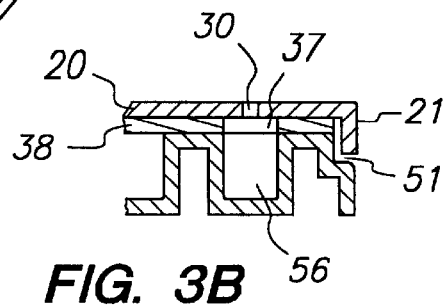
FIG. 3B

APPARATUS AND METHOD FOR TRANSFERRING LIQUIDS

This application claims benefit of Provisional Application Ser. No. 60/059,333 filed Sep. 19, 1997.

BACKGROUND OF THE INVENTION

1. Field of the Invention

This invention relates generally to methods and apparatus employing a plurality of transfer elements for multiplexing transfer of droplets of sample from multiwell source plates to surfaces reservoirs such as in miniaturized cassettes, in which chemical syntheses and analyses are possible. The invention is useful for the generation of combinatorial libraries and high throughput screening in, for example, pharmaceutical drug discovery, agricultural pesticide discovery, genomic science applications and the like.

2. Description of the Related Art

In a range of technology-based business sectors, including the chemical, bioscience, biomedical, and pharmaceutical industries, it has become increasingly desirable to develop capabilities for rapidly and reliably carrying out chemical and biochemical reactions in large numbers using small quantities of samples and reagents. Carrying out a massive screening program manually, for example, can be exceedingly time consuming and may be entirely impracticable where only a very small quantity of an important sample or component of interest is available, or where a component of a synthesis or analysis is very costly.

Accordingly, considerable resources have been directed to developing methods for high-throughput chemical syntheses, screening, and analyses. Considerable art has emerged, in part, from such efforts.

Automated laboratory workstations have contributed significantly to advances in pharmaceutical drug discovery and genomic science over the past decade. See for example, U.S. Pat. Nos. 5,104,621 and 5,356,525 (Beckman Instruments). More specifically, robotics technology has played a major role in providing a practical useful means for enabling high throughput screening (HTS) methods. Reference can be made, for example, to U.S. Pat. No. 4,965,049.

In addition to the emergence of automation technology, the last decade has seen an enormous advance in the scientific understanding of critical cellular processes, and this has led to rationally designed approaches in drug discovery. Also, the application of molecular genetics and recombinant DNA technology, U.S. Pat. No. 4,237,224 (Cohen and Boyer), has led to the isolation of many genes encoding proteins, which show promise as targets for new drugs. Once a target gene is identified, the recombinant protein can be heterologously expressed in mammalian tissue culture cells, insect cells, bacteria and/or, yeast.

The advantages of employing molecular cloning techniques are many. Often receptors and enzymes exist in alternative forms, subtypes or isoforms. Using a cloned target focuses the primary screen on the subtype appropriate for the disease. Agonists or antagonists can be identified and their selectivity can then be tested against the other known subtypes. The availability of such cloned genes and corresponding expression systems have enabled new types of screens to be created that are specific, sensitive, and often automatable.

Matched with the scientific and technological advances in biology has been the emergence of innovative methods for highly parallel chemical synthesis. For several decades, preparation of synthetic analogs to the prototypic lead compound was the established method for drug discovery. Natural products were usually isolated from soil microbes and cultured under a wide variety of conditions. The spectrum of organisms employed by the pharmaceutical industry for isolation of natural products has now expanded from Actinomycetes and fungi to include plants, marine organisms, and insects.

During the last five years, the chemistry of creating combinatorial libraries has made a vastly increased number of synthetic compounds available for testing. More specifically, thousands to tens or hundreds of thousands of small molecules can be rapidly and economically synthesized. See, for example, U.S. Pat. No. 5,252,743 (Affymax Technologies N.V.) for a discussion of combinatorial chemistry. Thus, combinatorial libraries complement the large numbers of synthetic compounds available from the more traditional drug discovery programs based, in part, on identifying lead compounds through natural product screening.

Competitive binding assays, originally developed in the 1960's for immunodiagnostic applications, continue to be commonly employed for quantitatively characterizing receptor-ligand interactions. Despite advances in the development of spectrophotometric and fluorometric-based bioanalytical assays, radiolabeled ligands are still commonly employed in pharmaceutical HTS applications. Although non-isotopic markers promise to be environmentally cleaner, safer, less expensive, and generally easier to use than radioactive compounds, sensitivity limitations have prevented these new methods from becoming widespread. Another major disadvantage of the competition assay is the number of steps, most notably, washing steps, required to run the assays.

A few years ago, Scintillation Proximity Assays were introduced by Amersham and also are discussed in U.S. Pat. Nos. 4,271,139 and 4,382,074 as a means of circumventing the wash steps required in the above heterogeneous assays. The new homogeneous assay technology, which requires no separation of bound from free ligand, is based on the coating of scintillant beads with an acceptor molecule, for example, the target receptor.

Another variation of this theme avoids the use of radioactivity and is especially useful in high-throughput assays. The modification involves the use of lanthanide chelates in time-resolved fluorometry. Aspects of this particular homogeneous assay technology are discussed in U.S. Pat. No. 5,637,509. This particular technology takes advantage of the unique properties of the lanthanide chelate europium-cryptate in combination with the energy absorbing molecule, allophycocyanin (APC).

Robotic-based high-throughput tools are now routinely used for screening libraries of compounds for the purpose of identifying lead molecules for their therapeutic potential. Subsequently, considerable art has emerged. For example, a screening method for characterizing ligand binding to a given target employing a variety of separation techniques is described in the PCT application WO 97/01755. Another related method is described in U.S. Pat. No. 5,585,277 (Scriptgen Pharmaceuticals).

Highly parallel and automated methods for DNA synthesis and sequencing have also contributed significantly to the success of the human genome project to date. For example, PE/Applied Biosystems (ABI), PerSeptive BioSystems, Pharmacia Biotech, and Beckman Instruments have developments in DNA synthesis instrumentation. In the area of DNA sequencing, ABI and LiCor are active. In addition, see U.S. Pat. No. 5,455,008. For a related invention, see Genzyme Corporation's HTS method for DNA analysis that is described in U.S. Pat. No. 5,589,330. For sequencing by hybridization, see PCT WO 89/10977 (Southern), Affymetrix (U.S. Pat. Nos. 5,599,695 and 5,631,734), and U.S. Pat. No. 5,202,231 (Drmanac, et al.).

Computerized data handling and analysis systems have also emerged with the commercial availability of high-throughput instrumentation for numerous life sciences research and development applications. Commercial software, including database and data management software, has become routine in order to efficiently handle the large amount of data being generated. Bioinformatics has emerged as an important field.

With the developments outlined above in molecular and cellular biology, combined with advancements in combinatorial chemistry, there has been an exponential increase in the number of targets and compounds available for screening. In addition, many new genes and their expressed proteins will be identified by the Human Genome project and will therefore greatly expand the pool of new targets for drug discovery. Subsequently, an unprecedented interest has arisen in the development of more efficient ultrahigh throughput methods and instrumentation for pharmaceutical and genomic science screening applications.

In recent parallel technological developments, miniaturization of chemical analysis systems, employing semiconductor processing methods, including photolithography and other wafer fabrication techniques borrowed from the microelectronics industry, has attracted increasing attention and has progressed rapidly. The so-called "lab-on-a-chip" technology enables sample preparation and analysis to be carried out on-board microfluidic-based cassettes. Moving fluids through a network of interconnecting enclosed microchannels of capillary dimensions is possible using electrokinetic transport methods.

Application of microfluidics technology embodied in the form of analytical devices has many attractive features for pharmaceutical high throughput screening. Advantages of miniaturization include greatly increased throughput and reduced costs, in addition to low consumption of both sample and reagents and system portability. Implementation of these developments in microfluidics and laboratory automation hold great promise for contributing to advancements in life sciences research and development.

Nonetheless, the 96 well microtiter plate and multiples thereof such as, e.g., the 384 well microtiter plate, have been, and still are, the pharmaceutical industry standard for carrying out bioanalytical assays despite the recent advances in miniaturization and microfluidics. Because an enormous number of synthetic libraries have been, and continue to be, generated using this particular multiwell format, the microtiter plate will remain entrenched within the industry.

As microfluidic technologies advance, new methods for enabling fluid transfer between multi-well plates and microassay cassettes would be beneficial. A critical factor currently limiting such a microfluidic HTS hybrid device is a means for reproducible liquid communication between the disparate dimensions of the two systems. More specifically, integration of microfluidics technology with existing robotic-based methods currently used in automated workstations is constrained by differences in volume size of samples used. For these reasons, new automated methods for multiplexing common lab tasks such as sample handling and dispensing on the microscale are required. Once again, other parallel developments, in this case borrowed from the ink jet printing industry, are applicable to fulfilling, at least in part, this currently unmet technological need. The art is briefly reviewed.

Various droplet ejector technologies have been or are being developed. One such technology, electrostatic discharge, is commonly used for dispensing fluids and reference may be made to U.S. Pat. Nos. 4,749,125; 5,086,973; 5,165,601 issued to Terronics Development Corp.; and U.S. Pat. No. 5,332,154 to Lundy and Associates.

Other devices use electrostatic energy to eject ink onto a recording medium. For a more detailed description of electrostatic ink printing, reference may be made to U.S. Pat. No. 5,588,597 to MicroParts GmbH; U.S. Pat. No. 5,278,583 to Matsushita Electric Industrial Co.; U.S. Pat. No. 4,915,718 to On Target Technology, Inc.; and U.S. Pat. No. 4,799,068 to Fuji Xerox Co., Ltd.

Another related invention includes Quate's acoustic fluid ejector system as described in U.S. Pat. No. 5,608,433 issued to Xerox Corp. Other related U.S. Patents include U.S. Pat. No. 5,586,723 issued to Spraying Systems Co.; U.S. Pat. No. 5,164,740 issued to Yehuda Ivr, and the citations therein.

Another ejector technology, piezoelectric ejection, is discussed in U.S. Pat. No. 5,164,740. For a more detailed description of piezoelectric printing, reference may be made to U.S. Pat. No. 5,529,055 issued to L'Oreal and the citations therein.

An apparatus for liquid transfer has been made and used for delivering a plurality of samples in sequence to treatment reservoirs wherein a chemical reaction or physical treatment step occurs. See, e.g., U.S. Pat. No. 5,188,148 for a conduit plate for fluid delivery system and U.S. Pat. No. 5,325,889 for a laminated conduit plate for fluid delivery system (both issued to Millipore Corp.).

Aspiration devices involve pneumatic forces or back pressure for its mechanism of action. See, e.g., U.S. Pat. No. 5,463,910 for a multi-function aspirating device (AVL Scientific Corp.); U.S. Pat. No. 5,384,093 for an apparatus for aspirating and discharging a liquid sample (Toa Medical Electronics Co., Ltd.); and U.S. Pat. No. 5,525,302 for a method and device for simultaneously transferring plural samples.

A multiwell plate is disclosed in PCT WO 97/15394 published May 1, 1997 (SmithKline Beecham Corporation). The wells have a large opening at the top and small nozzle hole in the base. The opening is chosen so that a jet of liquid is emitted when a pressure pulse is applied to the surface such that by selecting a time for the pressure pulse a precise amount of volume in the well can be dispensed.

SUMMARY OF THE INVENTION

One aspect of the present invention is a device comprising a plate having a plurality of transfer elements. Each of the transfer elements comprises an aperture in the plate where the aperture is capable of being electrically activated. The plate has one or more attaching elements for attaching the plate to a multiwell plate to form a sealed system except for the apertures of the transfer elements. Usually, the device is adapted for sealing attachment to a multiwell plate.

Another embodiment of the present invention is an apparatus for transferring liquid. The apparatus comprises a first plate comprising a plurality of individual wells containing the liquid. The wells rae formed in the first plate on a first side thereof wherein the second side of the plate is free of holes. The apparatus also comprises a second plate comprising a first side and a second side and a plurality of transfer elements comprising apertures in the second plate. Each of the apertures is capable of being electrically activated. The second plate is adapted for simultaneously transferring precise amounts of a liquid from the first plate to a sample receiving plate by electrically activating the apertures. The second side of the second plate is sealingly attached, and may be removably attached, to the first side of the first plate.

Another aspect of the present invention is a method for transferring liquid. A quantity of liquid is disposed to a second side of a plate having a plurality of apertures in the plate. The apertures are capable of being electrically activated. The liquid is present in a closed well except for the apertures in the plate. To simultaneously expel liquid through the apertures, the apertures are electrically activated.

Another aspect of the present invention is a method for transferring liquid. A first plate is used comprising a plurality of individual wells containing the liquid. The wells are formed in the first plate on a first side thereof. A second plate is also used. The second plate comprises a first side and a second side and a plurality of transfer elements, each comprising an aperture in the second plate. Each of the apertures is capable of being electrically activated. The second plate is adapted for simultaneously transferring precise amounts of a liquid from the first plate to a sample receiving plate by electrically activating the apertures. The second side of the second plate is sealingly attached, and may be removably attached, to the first side of the first plate. The apertures are positioned adjacent to an array of sample receiving reservoirs of a third plate, and the apertures are electrically activated.

Another aspect of the present invention is a method for transferring liquids. A multiwell plate is provided having liquid contained in the wells thereof. A second plate is provided and comprises a first side and a second side and a plurality of apertures. Each of the apertures is at least partially comprised of an electroconductive material. The second plate is attached to the multiwell plate such that each of the apertures is aligned with a corresponding well of the multiwell plate. The second plate comprises, on the second side, one or more attaching elements. The second plate is attached to the top of the multiwell plate by the attaching elements. The multiwell plate is attached to the second plate and the assembly is inverted so that liquid is disposed at each of the apertures. The dimensions and surface properties of the apertures are such that liquid does not exit the apertures under gravity conditions. The apertures are positioned adjacent to an array of sample receiving reservoirs of a microfluidic network in a third plate. Each of the microfluidic networks has an electrode connected to an electrode attached to the aperture. An electric potential is applied across the electroconductive material of the aperture and the opposing electrode establishing an electrostatic field that causes a portion of the liquid to exit the aperture as an electrospray and enter a corresponding sample receiving reservoir.

BRIEF DESCRIPTION OF THE DRAWINGS

FIG. 1 is a perspective view of one embodiment of the present invention.

FIG. 2A is a cross-sectional view of one of the transfer elements of the embodiment of FIG. 1.

FIG. 2B is a cross-sectional view of one of the transfer elements of an alternate embodiment of the present invention.

FIG. 2C is a cross-sectional view of one of the transfer elements of another alternate embodiment of the present invention.

FIG. 3A is a perspective view of one embodiment of the invention that includes attachment of the embodiment of FIG. 1 to a multiwell plate.

FIG. 3B is a cross-sectional view of a portion of the embodiment of FIG. 3A.

DESCRIPTION OF THE SPECIFIC EMBODIMENTS

Figure 4A:
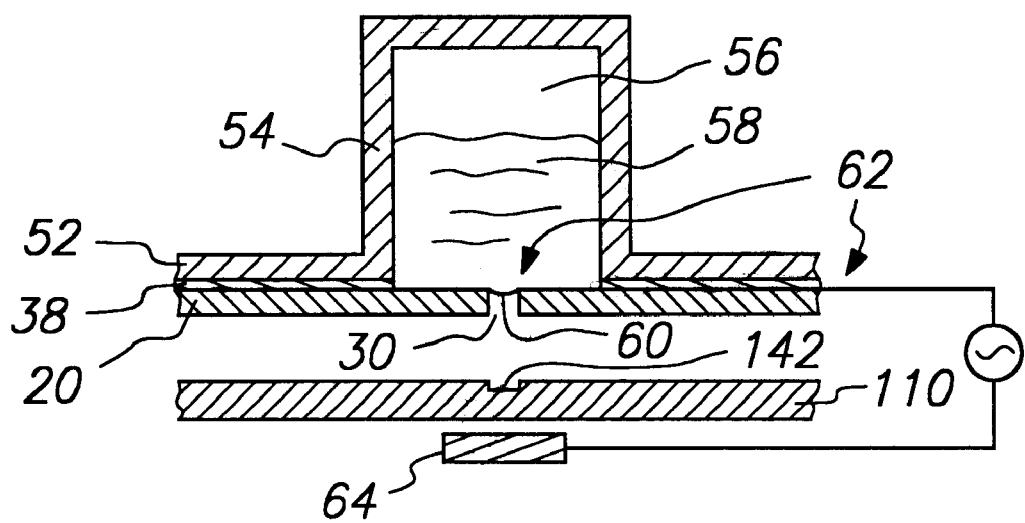
FIG. 4A is a cross-sectional view of one of the transfer elements and one of the wells of the embodiment of FIG. 3 and also includes a sample receiving reservoir of a third plate.

This invention encompasses methods and apparatus for multiplexing fluid transfer from multiwell source plates to sample receiving plates such as a planar surface or a sample receiving reservoir of a miniaturized cassette, in which chemical syntheses and analyses are possible. The invention provides a fluid application device for dispensing sample droplets to an array of spots on a planar surface or an array of receiving reservoirs on a microfluidic-based cassette from an array of sample wells. The invention further provides a means for enabling fluid transfer between the disparate dimensions associated with the size of a-sample reservoir (milliliter to microliter range) in, for example, a 96 or 384 well plate, and the volume of sample or reagents, (nanoliter to picoliter range) in a microfluidic device. The ability to achieve fluid communication in an automated manner across this so-called "macro-to-micro" transition is particularly useful for high throughput screening (HTS) applications, including pharmaceutical drug discovery and genomic science applications.

In one embodiment of the invention, sample handling is achieved by employing liquid-dispensing means housed within a protective cover assembly for the source plate. The cover assembly contains one transfer element for each well of the source or library plate, to which the assembly may be attached permanently or removably. The cover assembly device in its simplest concept is a cover plate comprising a plurality of nozzles that upon activation simultaneously dispense liquid droplets into the fluid—receiving sites of a microfluidic assay card. The mechanism of action of liquid transfer is electrical activation of the apertures. Accordingly, the transfer may be electrodynamically driver, including electrostatic spray or piezoelectric nozzles.

The sample-transfer devices of the present invention serve as a fluid-communication means for dispensing liquids having a volume ranging from microliters to nanoliters and potentially as small as picoliters, starting from samples in the milliliter to microliter range. Demand for having the capability to bridge the macro-to-micro transition has arisen from the emergence of microfluidic devices for use in HTS applications. Advantages of the invention as distinguished from conventional HTS include the elimination of wash steps, dead volume, carry-over and the significant reduction of contamination, in addition to being compatible with existing laboratory ware. For example, the sample transfer devices and methods of the invention serve as a hybrid system and are particularly well suited to integrating standard 96 and 384 multi-well sample plates with microfluidic network systems and corresponding robotic-based instrumentation for ultra-high throughput sample processing and analyses. The device of the present invention may be used with standard multiwell plates thereby avoiding the need for specialized plates. No special design is necessary for the multiwell plate. As will be appreciated by the skilled artisan, the present invention is quite versatile.

Before proceeding further with a detailed description of the present invention, a number of terms as used herein are defined.

Multiwell plate—a plate comprising an array of wells. The plate may have any number of wells, which are usually in a pattern, and are usually plates having 96, 192, 384 or 1536 wells or larger. Exemplary of such well plates are microtiter plates having a pattern of wells. The wells extend into the substrate forming the plate. The wells are open at the top surface of the plate and closed at the bottom surface thereof. There are no openings, holes or other exits from the wells other than from the top surface at the opening of the well.

Array—an arrangement of a plurality of elements such as a plurality of wells in a multiwell source plate, a plurality of apertures or nozzles in a sample transfer plate, a plurality of microfluidic networks on the multi-assay card, and so forth.

Planar array—an array that is arranged in a plane, which may be the plane of an object such as, for example, a planar substrate, comprising the array.

Microfluidic—of or pertaining to fluids and being of a magnitude on the order consistent with capillary dimension.

Microfluidic processing—processing carried out on a microfluidic scale. The processing involves fluid handling, transport and manipulation within chambers and channels of capillary dimension. Valveless sample injection is achieved by moving fluid from the reagent reservoirs into cross-channel injection zones, where plugs of buffer or test compounds are precisely metered and dispensed into a desired flowpath. The rate and timing of movement of the fluids in the various microchannels can be controlled by electrokinetic, magnetic, pneumatic, and/or thermal-gradient driven transport, among others. These sample manipulation methods enable the profile and volume of the fluid plug to be controlled over a range of sizes with high reproducibility. In addition, microfluidic processing may include sample preparation and isolation where enrichment microchannels containing separation media are employed for target capture and purification. Microfluidic processing may also include reagent mixing, reaction/incubation, separations and sample detection and analyses.

Microfluidic network—a system of interconnected cavity structures and capillary-size channels configured with a plurality of branches through which fluids may be manipulated and processed.

Cavity structure—an unfilled space with a mass, preferably, a hollowed out space in an object, such as, e.g., a planar substrate, a plate, or the like in accordance with the present invention such as, for example, a well, a reservoir, a chamber for incubation or separation or detection, and the like.

The cavity structures are usually present at one or both of the termini, i.e., either end, of a channel. The cavity structures may serve a variety of purposes, such as, for example, means for introducing a buffer solution, elution solvent, reagent rinse and wash solutions, and so forth into a main channel or one or more interconnected auxiliary channels, receiving waste fluid from the main channel, and the like.

Channels—a conduit or means of communication, usually fluid communication, more particularly, liquid communication, between elements of the present apparatus. The elements in communication are, e.g., cavity structures, and the like. Channels include capillaries, grooves, trenches, microflumes, and so forth. The channels may be straight, curved, serpentine, labyrinth-like or other convenient configuration within the planar substrate. The cross-sectional shape of the channel may be circular, ellipsoidal, trapezoidal, square, rectangular, triangular and the like so that it forms a microchannel within the planar substrate in which it is present.

The inside of the channel may be coated with a material for strength, for modifying, enhancing or reducing electroosmotic flow, for enhancing or reducing electrophoretic flow, for modification of surface hydrophobicity/hydrophilicity, for binding of selected compounds, and so forth. Exemplary of coatings are silylation, polyacrylamide (vinyl-bound), methylcellulose, polyether, polyvinylpyrrolidone, and polyethylene glycol, polypropylene, Teflon™ (DuPont), Nafion™ (DuPont), polystyrene sulfonate and the like may also be used. See also U.S. patent application Ser. No. 08/715,338, the relevant disclosure of which is incorporated herein by reference.

Capillary dimension—a cross-sectional area that provides for capillary flow through a channel. At least one of the cross-sectional dimensions, e.g., width, height, diameter, is at least about 1 $\mu$m, usually at least 10 $\mu$m, and is usually no more than 500 μm, preferably no more than 200 μm. Channels of capillary dimension typically have an inside bore diameter (ID) of from about 10 to 200 microns, more typically from about 25 to 100 microns.

Electroflow—the manipulation of entities such as molecules, particles, cells, vitreous fluid and the like through a medium under the influence of an applied electric field by use of electrodes and the like to induce movement such as electrokinetic flow, electroosmotic flow, electrophoretic flow, dielectrophoretic flow, and so forth. Depending on the nature of the entities, e.g., whether or not they carry an electrical charge, as well as the surface chemistry of the chamber in which the electroflow is conducted, the entities may be moved through the medium under the direct influence of the applied electric field or as a result of bulk fluid flow through the pathway resulting from the application of the electric field, e.g., electroosmotic flow. It is within the purview of the present invention that electroflow can be carried out in conjunction with movement of material by gravity or by application of a magnetic field, centrifugal force, thermal gradients, aspiration, negative pressure, pumping, pneumatic forces, and the like.

Electroflow medium—an electrically conductive medium; a medium generally utilized in carrying out microfluidic processes. The particular medium chosen is one that is suitable to a particular application of the present invention. Such media include, for example, buffer solutions, cross-linked and uncross-linked polymeric solutions, organic solvents, detergents, surfactant micellular dispersions, gels of the type generally used in connection with analytical separation techniques and other microfluidic processes, and so forth. For example, cross-linked polyacyrlamide gel, cellulose derivatives, uncross-linked polyacrylamide and derivatives thereof, polyvinyl alcohols, polyethylene oxides and the like may be used. For a discussion of such media see, e.g., Barron and Blanch, "DNA Separations by Slab Gel and Capillary Electrophoresis: Theory and Practice," Separation and Purification Methods (1995) 24:1–118.

The electroflow medium may be a conventional buffer such as, for example, the Good'buffers (HEPES, MOPS, MES, Tricine, etc.), and other organic buffers (Tris, acetate, citrate, and formate), including standard inorganic compounds (phosphate, borate, etc.). Exemplary buffer systems include: i) 100 mM sodium phosphate, pH 7.2; ii) 89.5 mM tris-base, 89:5 mM Boric acid, 2 mM ETDA, pH 8.3. Buffer additives include: methanol, metal ions, urea, surfactants, and zwitterions, intercalating dyes and other labeling reagents. Polymers can be added to create a sieving buffer for the differential separation of nucleic acids based on fragment length. Examples of such polymers are: polyacrylamide (cross-linked or linear), agarose, methylcellulose and derivatives, dextrans, and polyethylene glycol. Inert polymers can be added to the separation buffer to stabilize the separation matrix against factors such as convective mixing.

Alternatively, buffers containing micelles could be used for effecting separation of electrically neutral or hydrophobic substances of interest. The micelles are formed in the buffer by addition of an appropriate surfactant at a concentration exceeding the critical micelle concentration of that detergent. Useful surfactants include but are not limited to sodium dodecyl sulfate, dodecyltrimethyl ammonium bromide, etc. Weakly charged or apolar analytes partition into the micelles to different degrees depending upon their degree of hydrophobicity and thus can be separated. This subtechnique of capillary electrophoresis is termed micellar electrokinetic chromatography.

Electrophoresis—separation of components in a liquid by electroflow. Various forms of electrophoresis include, by way of example and not limitation, free zone electrophoresis, gel electrophoresis, isotachophoresis, high performance CE, capillary zone electrophoresis, and the like.

Electrophoresis column—in the context of the present invention, a channel for carrying out electrophoresis.

Electroforming—involves the electrodepositing of metal onto or into a mold or mandrel to produce a free standing metal object. The master pattern may be made from an original design or an actual article. The electrodeposition can be carried out to produce specified characteristics in the plated deposit. Various electroforming techniques are well-known in the art and will not be repeated here.

Electrical activation (electrically activated)—activation that is electrodynamically driven, including electrostatic activation, piezoelectric activation, and the like. Electrostatic activation is typically implemented by generating a 1.0 to 1.5 kV potential between a fluid reservoir with a nozzle or tip of target surface. Applied pulses of 0.5 to 1.0 kV can propel micron-sized droplets of picoliter volumes, or create continuous microstreams of 10 to 100 ml/hour. In the case of typical piezoelectric activation, picoliter to nanoliter droplets can be delivered at 1 kHz frequencies by cycling the deformation of a piezoelectric material via voltage modulation. Recent advances in high-frequency printing mechanisms have made it possible to deliver such droplets at 50 kHz frequencies by using a piezoelectric element to vibrate a microfabricated cantilevered beam with a tip that is in fluid communication with a liquid reservoir. For a further description of piezoelectric activation, see U.S. Pat. No. 5,164,740, the relevant disclosure of which is incorporated herein by reference.

Electroconductive material—material that is capable of transporting an electrical stimulus. Exemplary of such material are metals such as, e.g., nickel, copper, gold, silver, platinum, rhodium, palladium, and the like and alloys thereof such as, e.g., gold-copper alloy, palladium-nickel alloy, stainless steel, and so forth.

Planar surface—a planar surface is any generally two-dimensional structure on a solid substrate, which is usually rigid. The surface may be composed of any of a wide variety of materials, for example, polymers, plastics, resins, polysaccharides, silica or silica-based materials, carbon, metals, inorganic glasses, membranes, etc. The surface may be non-reactive to the liquid deposited thereon or it may contain reactive functionalities for binding to a component of the liquid. On the other hand, the surface may contain one or more reagents for conducting a chemical synthesis or analysis. The substrate upon which the surface lies may be composed of the same material as the surface. The substrate may have any convenient shape such as disk, square, and the like. Where the substrate is formed from a different material than the surface, the substrate may be formed from glass, modified silicon, polymeric material, such as polytetrafluoroethylene, polyvinylidenedifluoride or combinations thereof. Other substrate materials will be readily apparent to those of skill in the art upon review of this disclosure.

As mentioned above, one aspect of the present invention is a device comprising a plate having an array of transfer elements. The transfer elements comprise an array of apertures in the plate wherein each of the apertures is capable of being electrically activated. This is usually achieved by having at least a portion of the aperture comprise an electroconductive material. The configuration of the transfer elements generally conforms to the spacing format of the wells of a multiwell plate. The dimensions of the apertures are usually about 0.001 to 0.020 inches in diameter, preferably, about 0.005 to 0.01 inches in diameter.

Optionally, the area adjacent apertures in a plate may form a protrusion in the plate. Each protrusion corresponds to an aperture in the plate and extends the surface of the plate out of the plane of the plate. The protrusions from each of the apertures is generally tubular and of capillary dimensions.

It should be understood that the number of transfer elements associated with the plate may be less than the number of wells in a multiwell plate. For example, for a 96 well plate, the number of transfer elements in the transfer element plate may correspond to only one row of wells in the 96 well plate, i.e., 8 transfer elements in a single row. Several different transfer element plates may be employed independently of one another for the 96 well plate. Each of the transfer element plates may have a single row of 8 transfer elements where the single row in each corresponds to a different 8-well row of the 96 well plate. Other variations will be evident to those skilled in the art in view of the above disclosure. Thus, simultaneous transfer of liquids may be achieved for less than all of the wells in a multiwell plate.

The inner surface of the apertures and protrusions may be coated with a material that is conductive, preferably of higher conductivity than the liquid to be transferred and may be hydrophilic. In this regard the aperture, and/or the protrusion, may be formed from, or the inner surface thereof coated with, an electroconductive material. The apertures and/or protrusions may be coated with the electroconductive material by electroforming, sputtering, vacuum deposition, chemical deposition, electroplating, conductive inks, insert molding of conductive material such as stainless steel, and so forth. The transfer elements are designed to retain a quantity of liquid under normal conditions of gravity, vibration, handling, capillary action and the like. In other words the liquid does not exit the transfer elements until application of an external force. This feature is usually achieved by the design of the transfer elements. The apertures themselves, or the protrusions, may have any convenient shape such as, for example, circular, rectangular, oval, tubular, funnel-shaped, conical (varying diameter) or varying cross-sections such as truncated pyramid, and so forth. The protrusions can be tapered or straight. The protrusion is usually shaped in the form of a nozzle. The length of the protrusions is about 0.005 to 0.5 inches, preferably, about 0.05 to 0.10 inches, more preferably, about 0.050 inches. Usually, the length of the protrusions is related to the inner dimensions of the protrusion. Again, the overall consideration is that the liquid not exit the transfer elements until application of some force.

The exit orifice of the aperture or protrusion has an effect on the quality of the dispensation of the liquid from the transfer elements. In general, the smaller the diameter of the exit orifice, the smaller the volume of the drop of liquid ejected through the transfer elements. The dimensions of the exit orifice also have a large influence on the linear velocity of the dispensed liquid. The linear velocity must not be so great as to cause excessive splashing. In general, the exit orifice has dimensions of about 0.001 to 0.020 inches, preferably, about 0.003 to 0.010 inches, more preferably, about 0.005 inches.

The physical properties of the liquids to be dispensed also play a role in the composition, dimensions and geometry of the transfer elements. The composition of the transfer elements must be compatible with the liquid. Where the liquid contains particulate material, the dimensions of particularly the exit orifice must be such as to avoid clogging of the transfer element. Also of consideration are the viscosity, surface tension and density of the liquid to be transferred. As the viscosity of a liquid increases, the minimum dispensable volume achievable generally also increases. Surface tension has most impact on formation of droplets and the ability of the liquid to adhere to the protrusion. In general, as surface tension increases, the ability to dispense reliably also increases. Density has primary influence on the kinetic energy of the droplet. Generally, the greater the density, the greater the kinetic energy of the droplet. For the most part the particular parameters for the transfer elements may be determined empirically taking into consideration the above comments.

As will be appreciated, the volume of the liquid that enters the aperture and that is transferred from the multiwell plate to a sample receiving plate is determined, among others, by the dimensions of the apertures and the surface tension properties of the liquid and the surrounding area of the aperture and of the microwell plate. The liquid to be transferred is disposed adjacent to the apertures. In this regard the liquid may fill all or only a portion of the apertures. Furthermore, the liquid may simply form a meniscus at the opening of the aperture where the meniscus is convex at the opening of the aperture at which it is disposed and, thus, extends partially into the aperture. When liquid enters the aperture and/or protrusion, the volume of liquid that is usually about 0.1 nanoliter to about 2.5 microliters. The dimensions of interest for the apertures are primarily the inner dimension and the length. Retention of a certain volume of sample in the apertures is also dependent on the nature of the inner surface of the apertures. Accordingly, the inner surface of the apertures, and/or the protrusions, may be made hydrophobic or hydrophilic as desired.

The device is generally adapted for sealing attachment, optionally, removable attachment, to a multiwell plate. Removable attachment may be achieved by utilizing one or more attaching members, each corresponding to a well of a muiltiwell plate. The attaching members may also serve as positioning elements by assuring the alignment of the transfer elements with the wells of the multiwell plate when the present device is attached to the multiwell plate. The attaching element not only serves to secure the device to the multiwell plate, it may also provide for a sealing attachment. It is important that a proper seal be formed when the device is attached to the multiwell plate. When the plate is manipulated such as by inverting the plate to position the transfer elements, the liquid in the wells must not exit the wells except from the transfer elements and only upon activation. The attaching elements may be friction members, adhesive layer, press fit, and the like.

The friction members may be constructed from elastomeric material such as rubber including soft rubber, which may be natural or synthetic, including styrene-butadiene rubber; neoprene and nitrile rubbers; butyl, epichlorohydrine, ethylene-propylene rubbers; polyurethane rubbers; silicone and fluorosilicone rubbers; fluorocarbon rubbers; and so forth, as well as some other suitable material such as, e.g., low hardness thermoplastic materials, such as polyether- and polyester-based polyurethanes, polyvinyl chloride and fluoroelastomers. Alternatively, removable attachment may be achieved using materials such as ceramics, plastics, rubbers, and the like coated with a material that imparts slidability such as Teflon and the like.

One of the particularly advantageous features of the present invention is that the device and the microwell plate may be reused after washing. Thus, for this embodiment the device is attached to the multiwell plate, samples are transferred to a sample receiving plate in accordance with the present invention, the device is detached from the multiwell plate and the device and the microwell plate are washed for reuse. However, another advantage of the invention is that the device may be disposed of conveniently while the multiwell plate may be washed and reused.

In another aspect the apparatus comprising a microwell plate with the attached device in accordance with the present invention may be used to transfer liquids to a sample receiving plate. Thereafter, the apparatus may be stored for a period of time and then another aliquot of liquid transferred. This process can be repeated a number of times depending on the volume of liquid available in wells of the microwell plate. In this approach it is convenient to have a cover for the device of the present invention. This cover can be removably attached to the device opposite to the attached microwell plate. In this way the contents of the microwell plate may be incubated or the apparatus simply stored in a cold room until another transfer is desired. Such a cover may be conveniently made of plastic or other suitable material and is generally of a size corresponding to the size of the device. The cover may have sides that slip over at least a portion of the sides of the apparatus.

There may be one or several attaching elements per transfer element depending on the design of the attaching elements. For example, the attaching element may be a circumferential lip extending from a side of a plate opposite the side from which the protrusions extend. Alternatively, the attaching element may comprise several fingers depending from such side of the plate. Thus, the friction members may be in the form of a gasket, finger elements, preformed film and so forth. The friction member may be secured to the transfer element plate by physical adherence or permanent bonding using standard adhesive technology.

In another approach the attaching element providing for sealing attachment may be a non-permanent removable adhesive layer. The adhesive must be capable of providing a liquid tight seal with the top surface of the multiwell plate and must not be reactive with, or detrimental to, any component of the liquid in the wells of the multiwell plate. Suitable adhesives for forming an adhesive layer that provides for removing attachment include adhesives that are generally flexible, tacky, low cross-link density, pressure sensitive, and the like. Such adhesives include, for example, acrylic based, e.g., methacrylates, cyanoacrylates, etc., elastomeric, e.g., Neoprene, nitriles, polyurethanes, silicones, polysulfides, etc., plasticized hot melt, e.g., polyamides, polyesters, polyethylenes, polysulfones, vinyl acetates, etc. and the like. On the other hand the adhesive may be permanent and non-removable such as, for example, acrylic-based, epoxies, hot melt, elastomeric and so forth including some of the above where increased permanency is obtained by selecting for less flexibility and providing longer curing times.

It is also within the purview of the present invention that the adhesive layer be an adhesive coated on a support plate that is secured to the transfer element plate. The support plate may be a generally planar substrate fabricated from one or more of the materials mentioned above with respect to the friction members. Other examples of ways in which sealing attachment of the device to a multiwell plate may be realized include thermal bonding, clamping mechanisms, and so forth.

When the device of the present invention is attached to the top of a multiwell plate by means of the attaching elements, a sealed system is formed except for the apertures in the present device. Thus, attachment of the present device to a multiwell plate produces a closed chamber with the only exit port being that provided by a transfer element in accordance with the present invention.

The present device may be fabricated as a unitary plate or it may be constructed from several parts assembled into the device. For example, the plate may be made from plastic, plastic coated with an electroconductive material, an electroconductive material alone, and the like. The array of apertures may be made in the plate by laser cutting, etching, piercing, drilling, punching, direct molding or casting from a master with pins, and so forth.

Where the transfer element includes a protrusion, the protrusions are formed in the plate by means of electrical plating, electroforming, stamping and the like. The protrusions may be separately attached to the plate adjacent to the apertures. In the latter situation the protrusions may be of an electroconductive material and are preformed in the desired shape, e.g., nozzle, tapered nozzle, conical nozzle and so Separately formed protrusions may be attached to one side of the plate by suitable bonding means such as, e.g., adhesives, press fits, and so forth.

The other side of the plate has one or more attaching elements for attaching the plate to a plate comprising a plurality of sample containers such as a multiwell plate. If the attaching element is an adhesive layer, tacky material, or the like, the side of the plate bearing the adhesive layer or tacky material is covered with a suitable removable backing such as, for example, non-sticking plastic sheets, wax paper, and the like. The plate usually is about the same size as the multiwell plate to which it is attached. Typically, a standard 96 well plate is about 3.4 inches in width, about 5.0 inches in length, and about 0.6 inches in thickness. The thickness of the plate generally depends on the particular construction of the plate. It should be obvious that the dimensions of the plate are not critical as long as the dimensions are compatible with the microwell plate.

For applications where it is desired to have a disposable device, due to ease of manufacture and cost of materials, at least part of the device typically is fabricated from a plastic. Particular plastics finding use include polypropylene, such as high density polypropylene, polymethylmethacrylate, polycarbonate, polyethylene terephthlate, polystyrene or styrene copolymers, and the like. Of course, at least part of the aperture, or any protrusion, should be fabricated from, or coated with, an electroconductive material.

The device may be fabricated using any convenient means, including conventional molding and casting techniques. For example, a planar or flat plastic plate is injection molded with an array of countersunk apertures in a pattern corresponding to that of the wells in a microwell plate. In one approach an electroconductive material is electroformed on part or all of the inner surface of the aperture. Metal nozzles may be electroformed to the underside of the aperture locations.

In addition, production techniques used in flexible circuitry fabrication can be employed. Such fabrication techniques include conductive ink printing, imaging and etching or mechanically cutting metal foils, or forming and placing wire by numerical control (NC) equipment. The dielectric layers are tightly bonded to the conductive pattern using lamination techniques.

In one embodiment, once the apertures have been formed in the plate, an adhesive layer is applied to one side. The adhesive layer has through-holes having essentially the same centers as the apertures in the plate. However, the diameter of the through-holes of the adhesive layer are larger than that of the apertures and usually will approximate the diameter of the sample containers such as the wells of a multiwell plate. The adhesive layer is usually about 0.01 to 0.5 mm in thickness. The through-holes in the adhesive may be formed by molding, laser cutting, and so forth. The adhesive layer has a removable backing that is placed over the entire area of the adhesive layer.

For attaching elements that are friction members, a single substrate sheet may be employed with the friction members formed thereon in an array corresponding to the wells of the multiwell plate.

An example of one device in accordance with the present invention is depicted in FIGS. 1–2. Device 100 comprises a plate 20 having an array of transfer elements 22. The transfer elements each comprise a aperture 30 in plate 20. Plate 20 has outer lip 21 extending upward from plate 20 and extending around the perimeter of plate 20. Above plate 20 is adhesive layer 38 and removable backing 26. Backing 26 is shown as a transparent material in FIG. 1; however, backing 26 may be translucent or opaque. An array of through-holes 37 are present in adhesive layer 38 generally corresponding in location and centered with respect to the array of apertures 30. Through-holes 37 usually have a diameter that is about the diameter of the top of the wells in a standard multiwell plate, usually, about 4 mm. It is evident that the diameter of the through-holes can be larger of smaller depending on the diameter of the wells in a non-standard multiwell plate.

An alternate embodiment of the present invention is shown in FIG. 2B wherein apertures 30 have a funnel shape resulting from a circumferential bevel 36. Bevel 36 results from circumferential tapering from the side wall 28 adjacent to aperture 30 to the top rim of aperture 30. Bevel 36 is at an angle of about 10 degrees to 45 degrees with respect to wall 28 of plate 20. The function of bevel 36 is to assist liquid into aperture 30 when the present device is utilized.

Another embodiment of the present invention is shown in FIG. 2C wherein transfer elements 22 comprise apertures 30 in plate 20, which has protrusion 32 adjacent each of apertures 30. Protrusion 32 forms a nozzle, thereby extending aperture 30 accordingly. Plate 20 also has circumferential bevel 39 adjacent the top of aperture 30. Bevel 39 generally corresponds to protrusion 32. Bevel 39 results from circumferential tapering from the side wall 28 adjacent to aperture 30 to the rim of aperture 30. Bevel 39 is at an angle of about 10 degrees to 45 degrees with respect to wall 28 of plate 20. The function of bevel 39 is to assist liquid into aperture 30 when the present device is utilized.

An apparatus 50 in accordance with the present invention is depicted in FIGS. 3–4. Backing 26 is removed from plate 20, which is then attached to the top 52 of multiwell plate 54 having an array of wells 56 containing liquid 58. Plate 20 is pressed firmly into place on the top of multiwell plate 54 so that outer lip 21 fits snugly into cut out area 51, which extends around the periphery of plate 54. Adhesive layer 38 is pressed firmly against the front side 52 of multiwell plate 54. The construction of plate 20 is such that each of the transfer elements 22 are aligned with a corresponding well 56 of multiwell plate 54. In general the apertures are aligned so that the apertures are substantially centered with respect to the top of wells 56.

Figure 5:
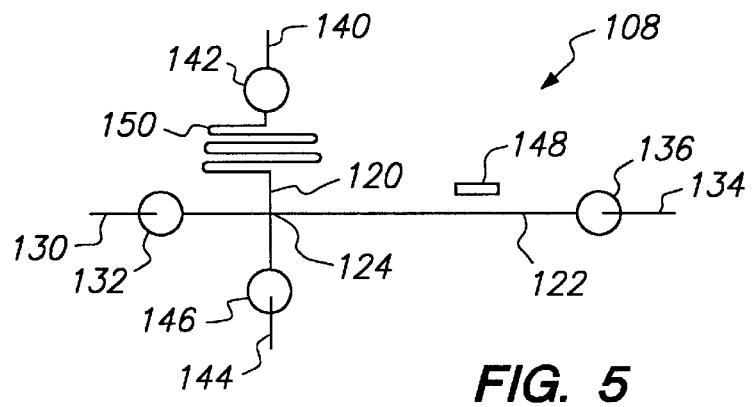
FIG. 5 is a perspective view of an embodiment of a microfluidic network.

Once device 100 is attached to multiwell plate 54, the resulting apparatus 50 is inverted so that each of the apertures 30 fills with liquid. A meniscus 60 is formed at opening 34. Apparatus 50 is, for example, then positioned adjacent to an array of sample receiving reservoirs 142, which are part of microfluidic networks 108 in a microfluidic network plate 110 as depicted in FIG. 5. Each of the microfluidic networks 108 has an electrode 64 connected to an electrode 62 attached to transfer element 22. An electric potential is applied to the electroconductive material means of electrodes 62 and 64 causing a precise amount of liquid 58 in each of transfer elements 22 to be forced out of the transfer elements and into a corresponding sample receiving reservoir 142.

Figure 4B:
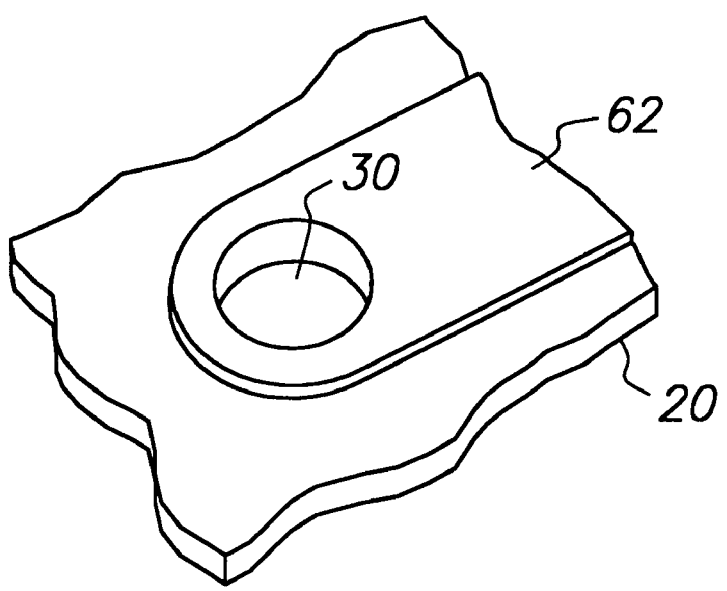
FIG. 4B is a perspective view of one of the transfer elements of the embodiment shown in FIG. 4A showing an electrode.

FIG. 4B shows the positioning of electrode 62 in the embodiment of FIG. 4A. Electrode 62 is shown adjacent aperture 30 of plate 20. In this depiction the electrode appears similar to a through-hole in a printed circuit board trace. The electrodes employed may be selected from those electrodes that are described more fully below with respect to the microfluidic networks.

The apparatus is disposed relative to the microfluidic network plate so that the transfer elements are aligned with the sample receiving reservoirs. As the number of samples in the array increases, alignment becomes more critical. A positioning device may be used to provide for precise alignment. Such device may be part of an instrument into which the present apparatus and the microfluidic network plate are inserted for activating the electroconductive material and for driving the electroflow in the microfluidic network plate. Positioning will generally be accomplished by mechanical, electromechanical, manual or similar means as is known in the art.

Alignment may also be affected by the forces acting on the droplet in flight from the exit orifice of the protrusion to the sample receiving reservoir. Air currents can alter the trajectory of the droplet. In addition, electrostatic charge differences between the droplet and the sample receiving plate can affect the path of the droplet. Consideration must be made of the above and the apparatus handled accordingly.

Figure 7:
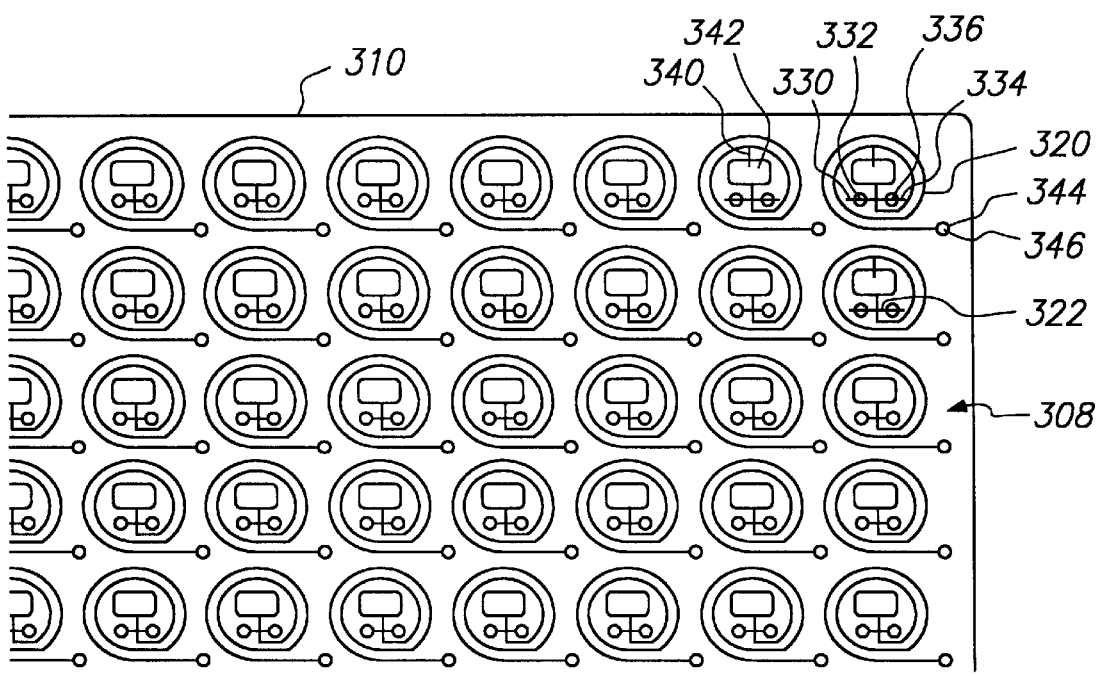
FIG. 7 is a perspective view of another embodiment of a portion of a plate having a plurality of microfluidic networks.

Microfluidic network plate 310 comprises an array of microfluidic networks 308 having interconnected cavity structures 342 and 346 and channels 320 (see FIG. 7). Each of the microfluidic networks corresponds to a respective sample transfer element 22 of device 100. The microfluidic network has interconnected cavity structures and channels, the latter forming one or more flowpaths resulting in an interconnected system. In general, there is a main flowpath and one or more secondary flowpaths. A desired microfluidic process may be carried out in the main flowpath or in one of the secondary flowpaths. The additional flowpaths may be employed for a variety of purposes such as, for example, enrichment of a sample, isolation, purification, dilution, and the like. A variety of configurations are possible, such as a branched configuration in which a plurality of flowpaths are in fluid communication with the main flowpath. See, for example, U.S. Pat. No. 5,126,022.

The main flowpath has associated with it at least one pair of electrodes for applying an electric field to the medium present in the flowpath. Where a single pair of electrodes is employed, typically one member of the pair is present at each end of the pathway. Where convenient, a plurality of electrodes may be associated with the flowpath, as described in U.S. Pat. No. 5,126,022, the relevant disclosure of which is herein incorporated by reference, where the plurality of electrodes can provide for precise movement of entities along the flowpath. The electrodes employed may be any convenient type capable of applying an appropriate electric field to the medium present in the flowpath with which they are associated.

An example of a basic configuration of a microfluidic network is shown in FIG. 5. Plate 110 is comprised of a plurality of microfluidic networks 108. Each network comprises main flowpath 120 and secondary flowpath 122, which intersect at 124. Electrode 130 is connected to reservoir 132 and electrode 134 is connected to reservoir 136. An electric potential can be applied to flowpath 122 by means of electrodes 130 and 134. Electrode 140 is connected to sample introduction port and reservoir 142 and electrode 144 is connected to reservoir 146. An electric potential can be applied to main flowpath 120 by means of electrodes 140 and 144. The main flowpath 120 has optional portion 150 that is tortuous to provide an appropriate path length and residence time to achieve mixing by diffusion, incubation, and so forth.

Secondary flowpath 122 has detection zone 148 where the result of a microfluidic process may be detected. For example, if the microfluidic process is an assay for an analyte, the detection zone permits the detection of a signal produced during the assay. Alternatively, if the microfluidic process is a chemical synthesis, the detection zone may be used to detect the presence of the synthesized compound. It is, of course, within the purview of the present invention to utilize several detection zones depending on the nature of the microfluidic process. There may be any number of detection zones associated with a single channel or with multiple channels. Suitable detectors for use in the detection zones include, by way of example, photomultiplier tubes, photodiodes, photodiode arrays, avalanche photodiodes, linear and array charge coupled device (CCD) chips, CCD camera modules, spectrophotometers, spectrofluorometers, and the like. Excitation sources include, for example, filtered lamps, LED'S, laser diodes, gas, liquid and solid state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. No. 5,560,811 (column 11, lines 19–30), U.S. Pat. Nos. 4,675,300, 4,274,240 and 5,324,401, the relevant disclosures of which are incorporated herein by reference. An example of an optical system for reading the channels in the detection zones comprises: a power supply, which energizes a photomultiplier tube. A power supply energizes a 75 watt Xenon lamp. Light from the lamp is condensed by focusing lens, which passes light to an excitation filter. A dichroic mirror directs excitation light to a microscope. The apparatus is mounted on a so that light passes over the channels. Fluorescent emission light is collected by the microscope, passed through a dichroic mirror, emission filter, spatial filter before reaching the photomultiplier (PMT). The output signal of PMT is fed to an analog-to-digital converter, which in turn is connected to computer.

Alternatively, a static detection system in which a stationary detection point some distance from the injection end of the capillary is monitored as bands to be analyzed traverse the length of the capillary and pass by the detection zone could be used. This type of detection could be implemented using optical fibers and lenses to deliver the excitation radiation to the capillary and to collect the fluorescent emission radiation from the detection zone in the capillary. Appropriate multiplexing and demultiplexing protocols might be used to sequentially irradiate and monitor a large array of capillaries using a single source and a single or a small number of photodetectors. Using this approach, each capillary in the array is sequentially polled to detect any analyte band in the detection zone of that capillary.

The detectors may be part of an instrument into which the present apparatus and the plates containing the microfluidic networks is inserted. The instrument may be the same instrument that comprises the electrode leads and other components necessary for utilizing the present apparatus. However, separate instruments may be used for housing a sample container plate, incubation of sample and reagents, detection of a result, electrical field application, and other operations such as temperature and humidity control, and so forth. Humidity control may be achieved in a number of ways such as, for example, the use of humidistats, water vapor sources confined in the device in fluid communication with other areas thereof, and so forth. Other methods of humidity control will be evident to those skilled in the art.

Generally, prior to using a microfluidic network a suitable electroflow medium as described above is introduced into the flowpaths defined by the channels in the secondary plate. The medium may be conveniently introduced through one of the reservoirs at the termini of each of the channels or directly into the channels themselves prior to sealing of a cover plate to the planar substrate.

The use of a microfluidic network is next discussed with reference to FIG. 5. Sample is introduced into sample introduction port and reservoir 142 together with appropriate reagents for carrying out a microfluidic process. An electric potential is applied across electrodes 140 and 144 causing medium containing the sample and other reagents to move through flowpath 120 and, in particular, portion 150 of 120. Mixing of sample and reagents, as well as incubation, take place in portion 150. When the portion of the medium containing the sample and reagents reaches intersection 124, the electric potential applied between electrodes 140 and 144 is discontinued and an electric potential is applied between electrodes 130 and 134. The point at which the sample and other reagents reach intersection 124 may be determined by detecting the presence of the sample or one of the reagents directly or by empirically determining the time at which the sample and reagents should reach the intersection 124, based on the particular nature of the sample, the medium employed, the strength of the electric potential and so forth. Application of the electrical potential to electrodes 130 and 134 causes a plug of medium of precise amount (determined by the dimensions of the channel) to move along secondary flowpath 122 towards reservoir 136 and through detection zone 148 where detection is conducted. This is the basic manner in which an exemplary microfluidic network operates. Of course, as will be appreciated by one of ordinary skill in the art, the precise manner of operation of microfluidic networks in an apparatus in accordance with the present invention is dependent on the construction of the apparatus. Considerations include, for example, whether reagents are present on board the apparatus or added from a source outside the apparatus. Other considerations include manipulation of beads or magnetic beads in the channels, filling of channels with buffer, manipulation of discrete drops within otherwise unfilled channels, method of fluid movement (electroosmotic, electrokinetic, surface tension, centrifugal, pneumatic), mixing two or more reagents, incubation, and so forth.

Those skilled in the electrophoresis arts will recognize a wide range of electric potentials or field strengths may be used, for example, fields of 10 to 1000 V/cm are used with 200–600 V/cm being more typical. The upper voltage limit for commercial systems is 30 kV, with a capillary length of 40–60 cm, giving a maximum field of about 600 V/cm.

There are reports of very high held strengths (2500–5000 V/cm) with short, small bore (10 microns) capillaries micromachined into an insulating substrate. Normal polarity is to have the injection end of the capillary at a positive potential. The electroosmotic flow is normally toward the cathode. Hence, with normal polarity all positive ions and many negative ions will run away from the injection end. Generally, the "end-of-capillary" detector will be near the cathode. The polarity may be reversed for strongly negative ions so that they run against the electroosmotic flow. For DNA, typically the capillary is coated to reduce electroosmotic flow, and the injection end of the capillary is maintained at a negative potential.

Figure 6:
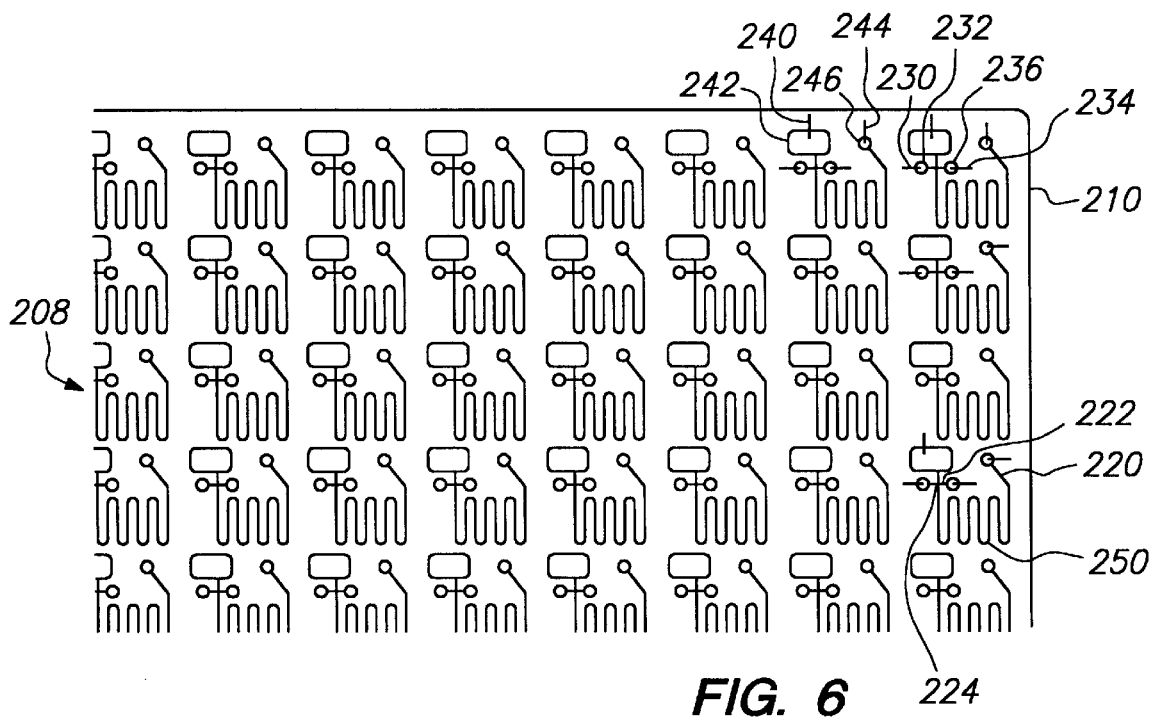
FIG. 6 is a perspective view of one embodiment of a portion of a plate having a plurality of microfluidic networks.
Figure 8:
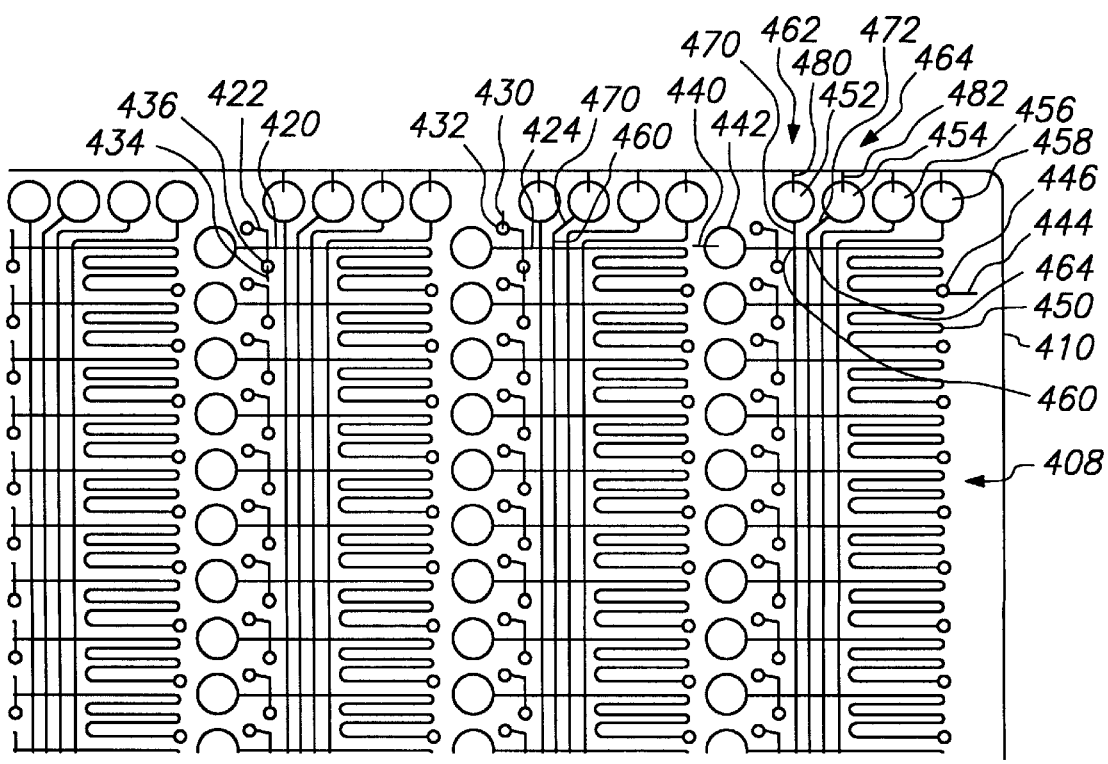
FIG. 8 is a perspective view of another embodiment of a portion of a plate having a plurality of microfluidic networks.

Examples of plates that are suitable for the microfluidic network plate apparatus are provided in FIGS. 6–8. Only a portion of the microfluidic network plates is shown in FIGS. 6–8. It is to be understood that the microfluidic network plates may have any number of separate networks including more than or less than 96. The number of microfluidic networks may be multiples of 96 where the number is greater than 96 or multiples of 8 where the number is less than 96. In addition, some of the features of the microfluidic networks are not shown in all of the networks depicted in FIG. 6–8.

In FIG. 6 a portion of a plate 210 is shown where the entire plate may have up to ninety six (96) microfluidic networks 208. Each network comprises main flowpath 220 and secondary flowpath 222, which intersect at 224. Electrode 230 is connected to reservoir 232 and electrode 234 is connected to reservoir 236. An electric potential can be applied to secondary flowpath 222 by means of electrodes 230 and 234. Electrode 240 is connected to sample introduction port and reservoir 242 and electrode 244 is connected to reservoir 246. An electric potential can be applied to main flowpath 220 by means of electrodes 240 and 244. The main flowpath 220 has a portion 250 that is in the form of a linear reciprocating coil to provide a tortuous path.

In FIG. 7 a portion of a plate 310 is shown where the entire plate may have up to ninety six (96) microfluidic networks 308. Each network comprises main flowpath 320 and secondary flowpath 322, which intersect at 324. Electrode 330 is connected to reservoir 332 and electrode 334 is connected to reservoir 336. An electric potential can be applied to secondary flowpath 322 by means of electrodes 330 and 334. Electrode 340 is connected to sample introduction port and reservoir 342 and electrode 344 is connected to reservoir 346. An electric potential can be applied to main flowpath 320 by means of electrodes 340 and 344. The main flowpath 320 is a circular coil to provide a tortuous path.

In FIG. 8 a portion of a plate 410 where the entire plate may have up to ninety six (96) microfluidic networks 408. Each network comprises main flowpath 420 and secondary flowpath 422, which intersect at 424. Electrode 430 is connected to reservoir 432 and electrode 434 is connected to reservoir 436. An electric potential can be applied to secondary flowpath 422 by means of electrodes 430 and 434. Electrode 440 is connected to sample introduction port and reservoir 442 and electrode 444 is connected to reservoir 446. An electric potential can be applied to main flowpath 420 by means of electrodes 440 and 444. The main flowpath 420 has a portion 450 that is in the form of a linear reciprocating coil to provide a tortuous path. The microfluidic networks of plate of FIG. 8 also comprise set of reagent reservoirs 452, 454, 456 and 458. Each of the reagent reservoirs has a channel providing communication between the reagent reservoir and each of the main flowpaths of the microfluidic networks. Accordingly, reagent reservoir 452 has a channel 470 that intersects main flowpath 420 at 460 for each of the microfluidic networks in row 462 of plate 410. Likewise, reagent reservoir 454 has a channel 472 that intersects main flowpath 420 at 464 for each of the microfluidic networks in row 464 of plate 410. The same situation exists for reagent reservoirs 456 and 458. Reagents are moved through channels 470 and 472 by means of application of electric potential at electrodes 480 and 482, respectively. By appropriate alternation of electric potential in channels 470 and 472 on the one hand and main channel 420 on the other, precise amounts of reagents can be metered into main flowpath 420.

With regard to electrodes, some or all of the electrodes may be within the second plate with external connections to power supplies that may be part of an instrument into which the present apparatus is inserted. On the other hand, some or all of the electrodes might be on a separate part (e.g. built into an instrument into which the present apparatus is inserted), such that the electrodes can be immersed into the appropriate fluid reservoirs at the time of use. In this approach the electrodes in the separate instrument may be adapted to make contact with an appropriate lead from each of the reservoirs forming a part of the microfluidic networks in the subject apparatus. The electrodes may be strip metal electrodes formed in a stamping process or chemical etching process. The electrodes may be wires or strips either soldered or glued with epoxy and can be made of conductive materials such as platinum, gold, carbon fibers and the like. The electrodes could be deposited, coated or plated onto a section of the exterior wall of a capillary near each end of the capillary. Controlled vapor deposition of gold, platinum, or palladium metal onto the exterior wall of the capillary is one method of forming the electrodes. This technique can be used to produce an electrode layer with a thickness up to several microns. Thicker electrodes could be subsequently formed by electrochemically plating gold, palladium or platinum onto the thin electrode formed by the vapor deposition process. Electrodes could be integral with the second plate formed by silk screening process, printing, vapor position, electrode-less plating process, etc. Carbon paste, conductive ink, and the like could be used to form the electrode. The electrodes may also be present between the plate comprising the transfer elements and the attaching element(s).

Regardless of the embodiment of the present invention that is constructed, it is preferable for the electrodes to be connected to an electronic computer. The computer has programmed software dedicated to providing the moving waves or voltage profile along the channel. Various different types of software can be provided so as to obtain the best possible results in the particular microfluidic processing conducted.

It is also within the purview of the present invention that the computer software that is connected to the electrodes be made interactive with an optical detection device such as ultraviolet or fluorescence spectrometer. The spectrometer can be focused singly or at various points along the medium in the channels. As the ultraviolet spectrometer reads different types of substances being moved to different portions of the medium, the information can be sent to the computer, which can adjust the speed of the waves or voltage distribution profiles being generated in order to more precisely fine tune the resolution of the substances being moved through the medium.

As mentioned above, the channels can be in any shape. More specifically the channels can be fashioned so that it has a plurality of branches. Each of the branches along with the channel itself can be filled with a desired medium. Various reagents may be moved along the branches by utilizing the moving electric wave generated by the computer. Accordingly, a sophisticated computer program may be utilized to provide for various protocols for microfluidic processing such as chemical synthesis, sequencing of polynucleotides.

The apparatus of the present invention may have any convenient configuration capable of comprising the device, the microwell plate and so forth and their respective component parts. The cavities and channels of the microfluidic network are usually present on the surface of a planar substrate where the substrate will usually, though not necessarily be covered with a cover plate to seal the microfluidic networks present on the surface of the planar substrate from the environment. The cover plate will have appropriate communication means for establishing communication between each of the sample receiving elements of the first plate and the corresponding microfluidic network of the second plate. Such means include, for example, through-holes, capillaries, porous wicks and the like. The apparatus may have a variety of configurations such as, for example, rectangular, circular, or other convenient configuration. Generally, apparatus in accordance with the present invention are of a size that is readily handled and manipulated. In general, a rectangular apparatus has dimensions of about 3 inches by 5 inches; a circular apparatus has a diameter of about 4 to 16 inches; and each would have a thickness of about 0.60 to 1.5 inches (including all of the elements of the apparatus). It should be obvious that the size of the present devices and apparatus is not critical and is in general a function of the particular multiwell plate with which the present device may be used.

The plate containing the microfluidic networks may be fabricated from a wide variety of materials, including glass, fused silica, acrylics, thermoplastics, (cross-linked) thermosets and the like. The various components of the plate may be fabricated from the same or different materials, depending on a number of factors such as, e.g., the particular use of the device, economic concerns, solvent compatibility, optical clarity, color, mechanical strength, selective strength, surface chemistry, method of production, and so forth. For example, the planar substrate of the microfluidic network may be fabricated from the same material as the cover plate, e.g., polymethylmethacrylate, or from different materials such as, e.g., polymethylmethacrylate for the substrate and glass for the cover plate.

For ease of detection and fabrication, the entire apparatus may be fabricated form a plastic material that is optically transparent, which generally allows light of wavelengths ranging from 180 to 1500 nm, usually 220 to 800 nm, more usually 450 to 700 nm, to have low transmission losses. Suitable materials include fused silica, plastics, quartz, glass, and so forth.

Also of interest as materials suitable for fabrication of microfluidic network plate are plastics having low surface charge under conditions or electroflow. Particular plastics finding use include polymethylacrylate, polycarbonate, polyethylene terephthlate, polystyrene or styrene copolymers, polyethylene, polypropylene, polybutadiene, Teflon, silicones, and the like.

The microfluidic network plates may be fabricated using any convenient means, including conventional molding and casting techniques. For example, with plastic material, a silica mold master which is negative for the network structure in the planar substrate of the second plate can be prepared by etching or laser micromachining. In addition to having a raised ridge which forms the channel in the substrate, the silica mold may have a raised area that provides for one or more cavity structures in the planar substrate. Next, a polymer precursor formulation can be thermally cured or photopolymerized between the silica master and support planar plate, such as a glass plate. Where convenient, the procedures described in U.S. Pat. No. 5,110, 514, the relevant disclosure of which is incorporated by reference, may be employed. After the planar substrate has been fabricated, the enrichment channel may be placed into the cavity in the planar substrate and electrodes introduced where desired. Finally, a cover plate may be placed over, and sealed to, the surface of the substrate. The cover plate may be sealed to the substrate using any convenient means, including ultrasonic welding, adhesives, etc.

In one approach the microfluidic network plates may have multiple layers that are sandwiched together similar to multiple layer electronic printed circuit boards. In this approach the plates may be made in a manner similar to the printed circuit boards. Each layer contains cavities, channels and through-holes. When the various plates are assembled into an apparatus, the channels and through-holes in each layer can interconnect forming three dimensional fluid circuits. This approach allows significantly greater circuit complexity and circuit density than the single layer approach.

Figure 9:
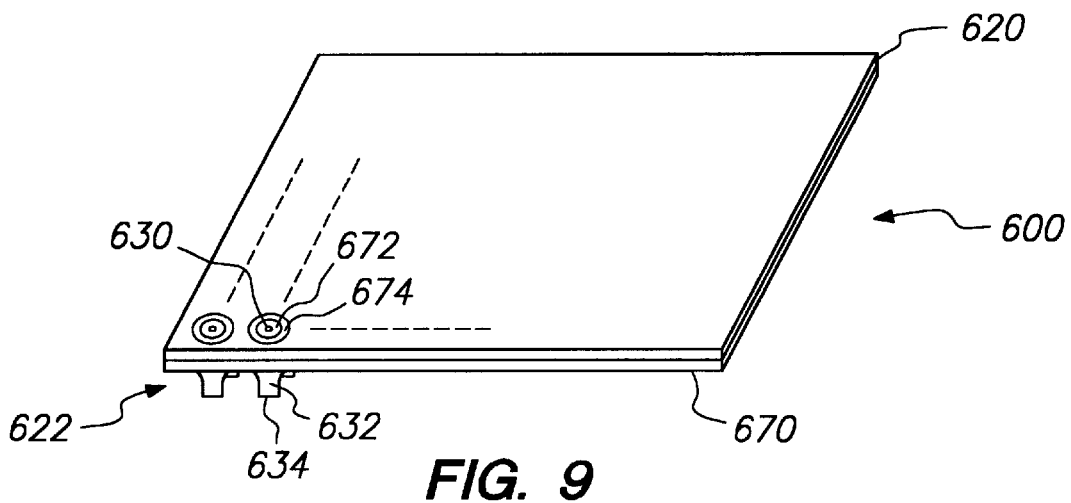
FIG. 9 is a perspective view of another embodiment of the present invention.
Figure 10:
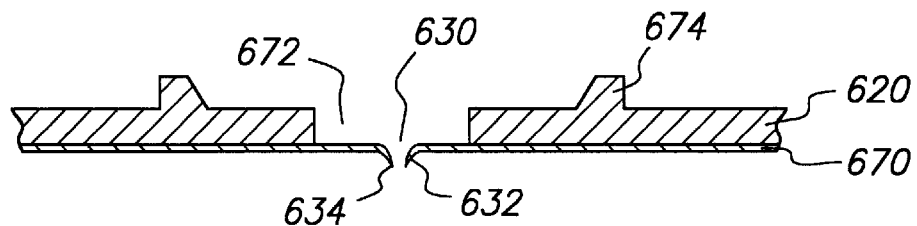
FIG. 10 is a cross-sectional view of one of the transfer elements of the embodiment of FIG. 1.
Figure 11:
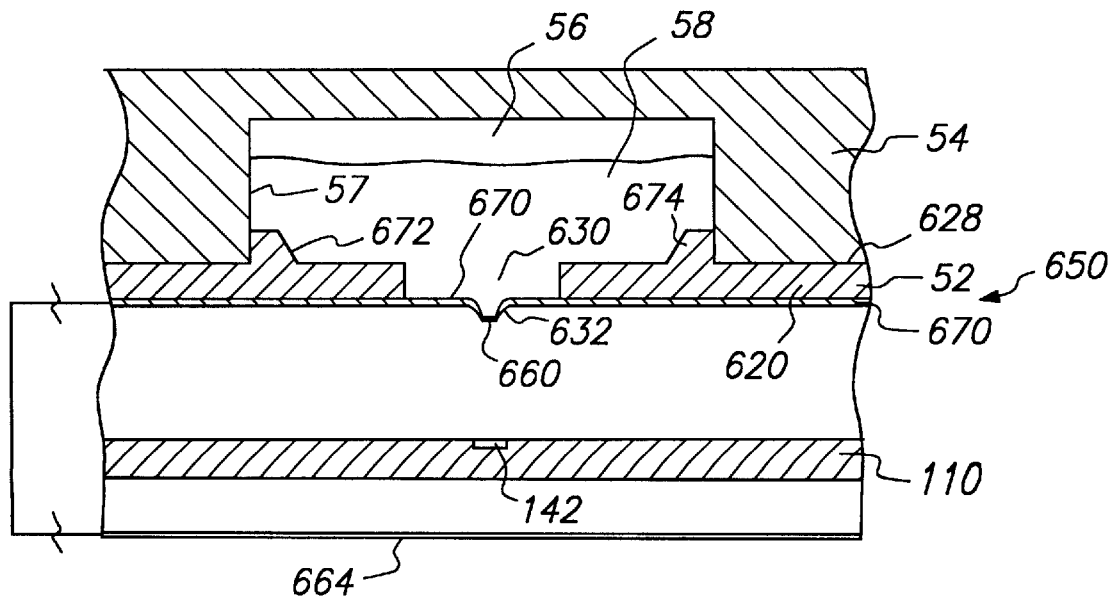
FIG. 11 is a cross-sectional view of one of the transfer elements of the embodiment of FIG. 9 wherein the embodiment of FIG. 9 is attached to a multiwell plate and further includes a sample receiving reservoir of a third plate.

Another embodiment of a device in accordance with the present invention is shown in FIGS. 9–11. Device 600 comprises a plate 620 having an array of transfer elements 622. Transfer elements 622 each comprise a aperture 630 in plate 620 with a protrusion 632 depending therefrom. In this embodiment protrusion 632 is formed in plate 670, which is permanently, non-removably attached to plate 620. Plate 670 is manufactured from an electroconductive material. Plate 670 is usually about 0.1 to about 10 mm in thickness, preferably, about 1 to about 5 mm in thickness. Typically, plate 670 is a thin metal foil secured to plate 620 and perforated in a precision manner to produce protrusions 632, which has opening 634. Plate 620 comprises circumferential opening 672 adjacent each of apertures 630. The function of opening 672 is to assist liquid into aperture 630 when the present device is utilized. The dimensions of opening 672 are about 0.1 to 5 mm in diameter, usually, about 1 to 4 mm in diameter. Plate 620 also comprises circumferential rib 674 adjacent opening 672 and in a direction generally opposite to protrusions 632. Rib 674 may be integral with plate 620, and thus formed from the same material as plate 620, or it may be formed from a different material and fixedly attached to plate 620. Rib 674 is used for providing sealing removable attachment of plate 620 to a multiwell plate 54. Thus, ribs 674 assist in positioning plate 620 with respect to multiwell plate 54 and aligning transfer elements 622 with wells 56. Ribs 674 are each about 1 to about 10 mm, preferably, about 5 to 10 mm, in length and about 0.2 to about 2 mm in thickness. Optionally, a removable backing (not shown) may be included to protect the ribs during shipment and handling.

As with the device of FIGS. 1–2, the device of FIGS. 9–10 is attached to the top 52 of multiwell plate 54 as shown in cross-section in FIG. 11. Plate 620 is pressed firmly into place on the top of multiwell plate 54. Ribs 674 are inserted into wells 56 and engage side walls 57 thereof resulting in a friction fit and sealing removable attachment to wells 56. Thus, the construction of plate 620 is such that each of the transfer elements 22 are aligned with a corresponding well 56 of multiwell plate 54.

Once device 600 is attached to multiwell plate 54, the resulting apparatus 650 is inverted so that each of the protrusions fills with liquid. A meniscus 660 is formed at opening 634. Apparatus 650 is then positioned adjacent to an array of sample receiving reservoirs 142, which are part of microfluidic networks 108 in a microfluidic network plate 110 as depicted in FIG. 11. Each of the microfluidic networks 108 has an electrode 664 connected to plate 670, of which transfer element 622 is comprised. An electric potential is applied across plate 670, which is made of conductive material means of electrode 664, which is connected to plate 670, causing a precise amount of liquid 58 in each of transfer elements 622 to be forced out of the transfer elements and into a corresponding sample receiving reservoir 142.

The embodiment of FIGS. 9–11 does not require an adhesive, and, thus, there is no adhesive to contact the liquid to be transferred. The embodiment relies on a press fit of the ribs 674 in the well of a microwell plate. Plate 670 may be fabricated inexpensively and eliminates the need to coat the aperture or nozzle with an electroconductive material.

Figure 12:
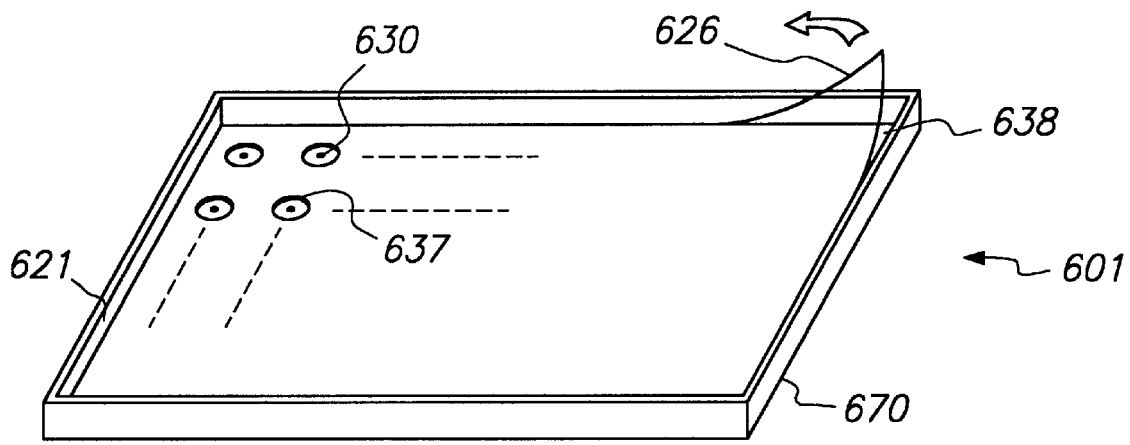
FIG. 12 is a perspective view of another embodiment of the present invention.
Figure 13:
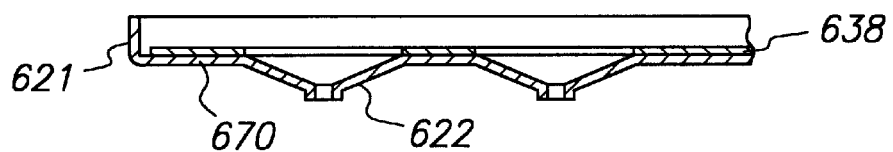
FIG. 13 is a cross-sectional view of one of the transfer elements of the embodiment of FIG. 12.
Figure 14:
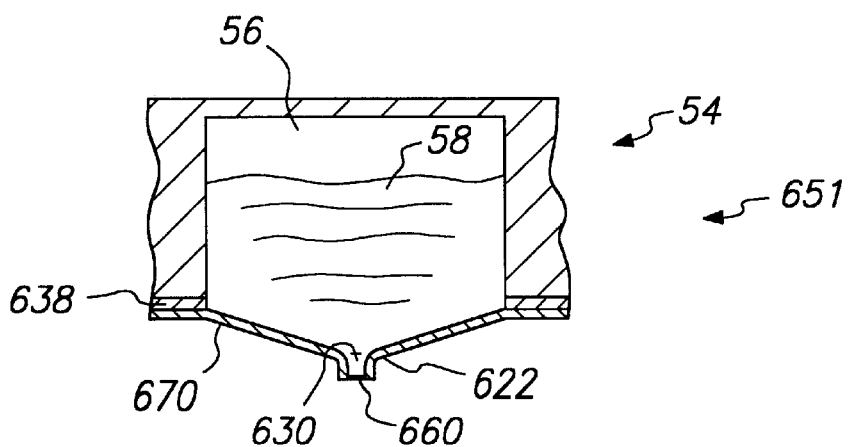
FIG. 14 is a cross-sectional view of the embodiment of the invention of FIG. 12 that includes attachment to a multiwell plate.

In an alternate embodiment depicted in FIG. 12–14 plate 670 may be composed of an electroconductive material in the form of a sheet with nozzle-like protrusions. The device depicted in FIGS. 12–14 has an adhesive layer 638 similar to that in the embodiment depicted in FIGS. 1–3 above. Adhesive layer 638 lies above plate 670 and removable backing 626 lies above 638. An array of through-holes 637 are present in adhesive layer 638 generally corresponding in location and centered with respect to the array of apertures 630.

In use, backing 626 is removed from plate 670, which is then attached to the top 52 of multiwell plate 54 having an array of wells 56 containing liquid 58. Plate 670 is pressed firmly into place on the top of multiwell plate 54 so that outer lip 621 fits snugly into cut out area 51, which extends around the periphery of plate 54. Adhesive layer 638 is pressed firmly against the front side 52 of multiwell plate 54. The construction of plate 670 is such that each of the transfer elements 622 are aligned with a corresponding well 56 of multiwell plate 54. Once device 601 is attached to multiwell plate 54, the resulting apparatus 651 is inverted so that each of the apertures 630 fills with liquid. A meniscus 660 is formed.

Figure 15:
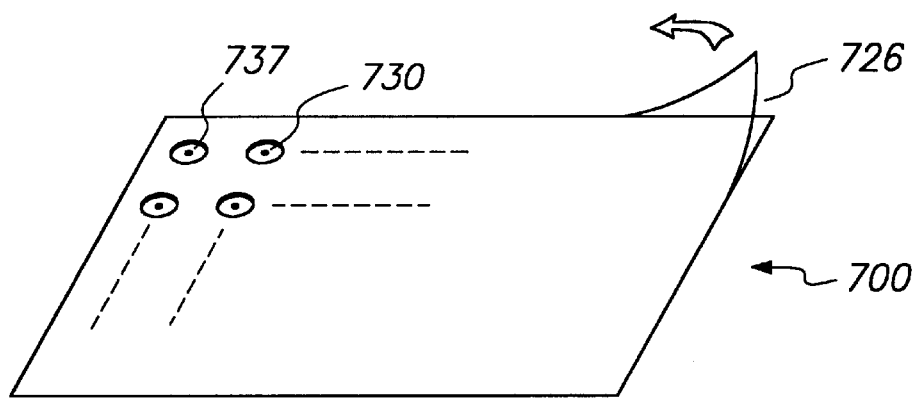
FIG. 15 is a perspective view of another embodiment of the present invention.
Figure 16:
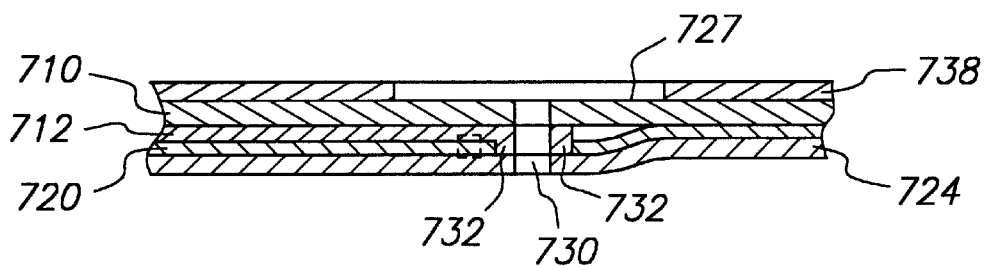
FIG. 16 is a cross-sectional view of one of the transfer elements of the embodiment of FIG. 15.
Figure 17:
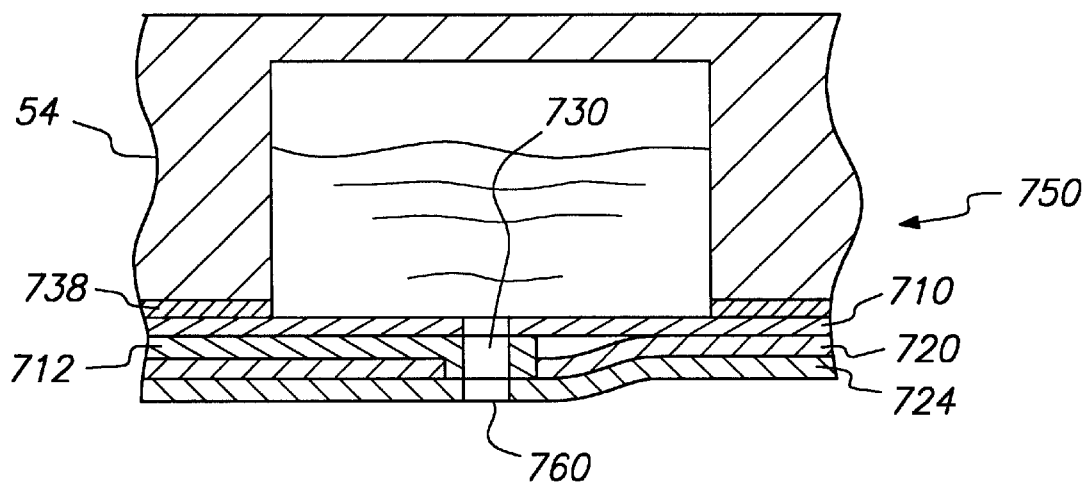
FIG. 17 is a cross-sectional view of the embodiment of the invention of FIG. 15 that includes attachment to a multiwell plate.

Another embodiment of the present invention is depicted in FIGS. 15–17. This approach is based on the use of flexible circuit technology. The device 700 comprises supporting film 710 to which conductive traces 712 are attached. Supporting film 710 may be fabricated from polymer films such as mylar, kapton, etc., and the like. Backing film 720 is layered below conductive traces 712, which extend to the inside surface of aperture 730 in backing film 720. Backing film 720 is fabricated from polymer films such as mylar, kapton, etc., and the like and has through-holes 730, which are plated with an electroconductive material at 732. Conductive traces 712 are printed conductive ink, vacuum deposited metal, plated metal, and the like. Below backing film 720 is cover film 724 with a through-hole corresponding to 730. Cover film 724 is fabricated from polymer films such as mylar, kapton, etc., and the like. Above supporting film 710 is adhesive layer 738 with opening 737, which is larger than, and centered on, through-hole 730. Above adhesive 738 is removable backing 726. The above device may be constructed in a manner similar to that disclosed in U.S. Pat. Nos. 4,626,462, 4,675,786 and 4,715,928, the relevant disclosures of which are incorporated herein by reference.

In use, backing 726 is removed from device 700, which is then attached to the top 52 of multiwell plate 54 having an array of wells 56 containing liquid 58. Adhesive layer 738 is pressed firmly against the front side 52 of multiwell plate 54. The construction of device 700 is such that each of through-holes 730 is aligned with a corresponding well 56 of multiwell plate 54. Once device 700 is attached to multiwell plate 54, the resulting apparatus 750 is inverted so that each of the apertures 730 fills with liquid. A meniscus 760 is formed.

Figure 18:
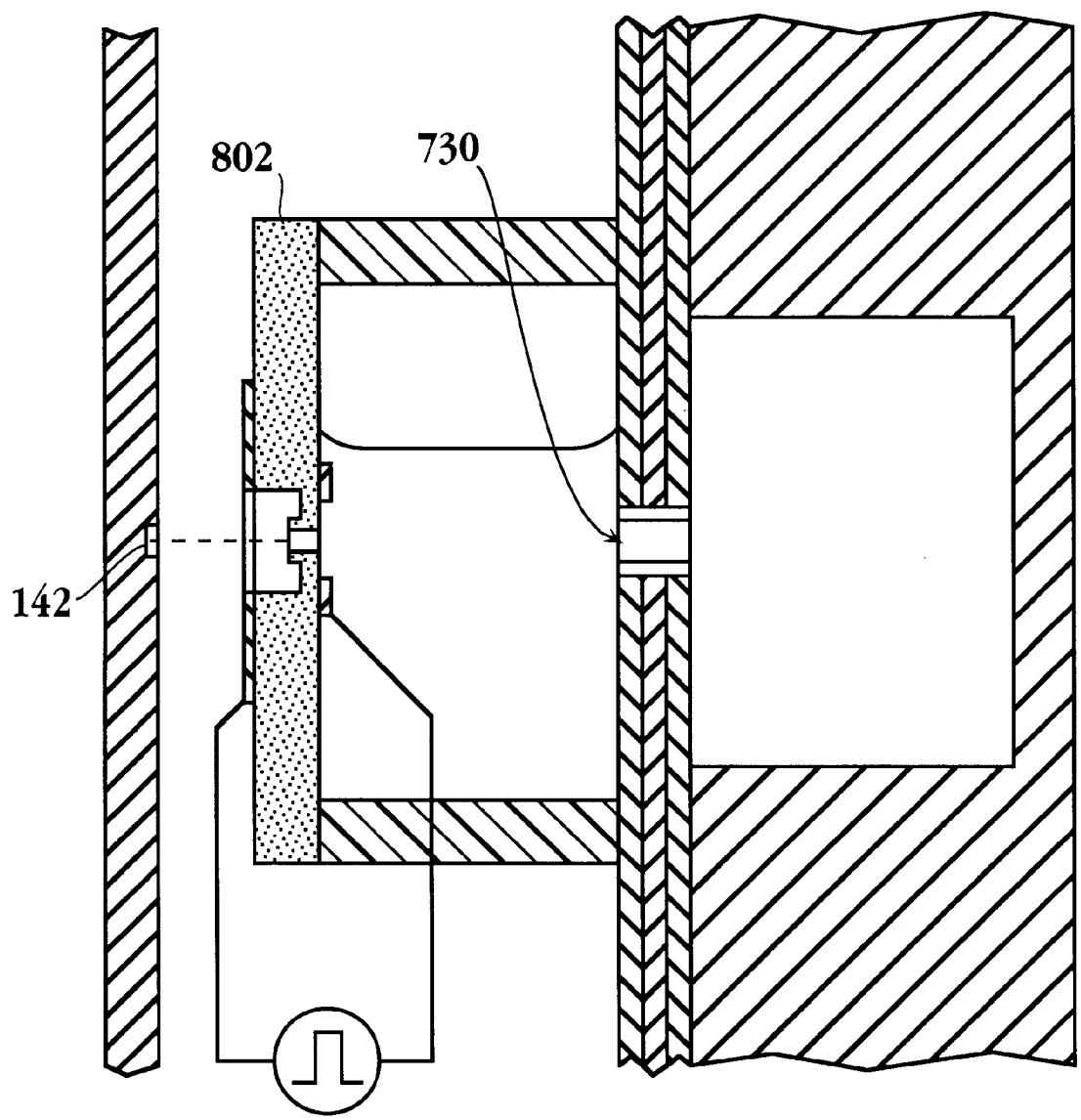
FIG. 18 is a cross-sectional view of an embodiment of the invention that includes an acceleration electrode.

VII. As shown in FIG. 18, an acceleration (or ring) electrode 802 may be used to assist in dispensing liquid where the distance between the aperture 730 and the sample receiving reservoir 142 may substantially affect the dispensing operation. Such acceleration electrodes have been used in other applications. See, for example, U.S. Pat. No. 5,278,583, the relevant portions of which are incorporated herein by reference. The acceleration electrode may be placed between the aperture and the sample receiving reservoir. If desired, a bias voltage can be applied between the electrode associated with the aperture and the electrode associated with the sample receiving reservoir. To cause dispensing of liquid, a pulsed voltage is applied between the acceleration electrode and the aperture, causing droplets to be accelerated out from the aperture towards the hole in the acceleration electrode. The timing of the pulse should be adjusted so that droplets are not inadvertently pulled sideways onto the acceleration electrode as they pass through the hole.

Figure 19:
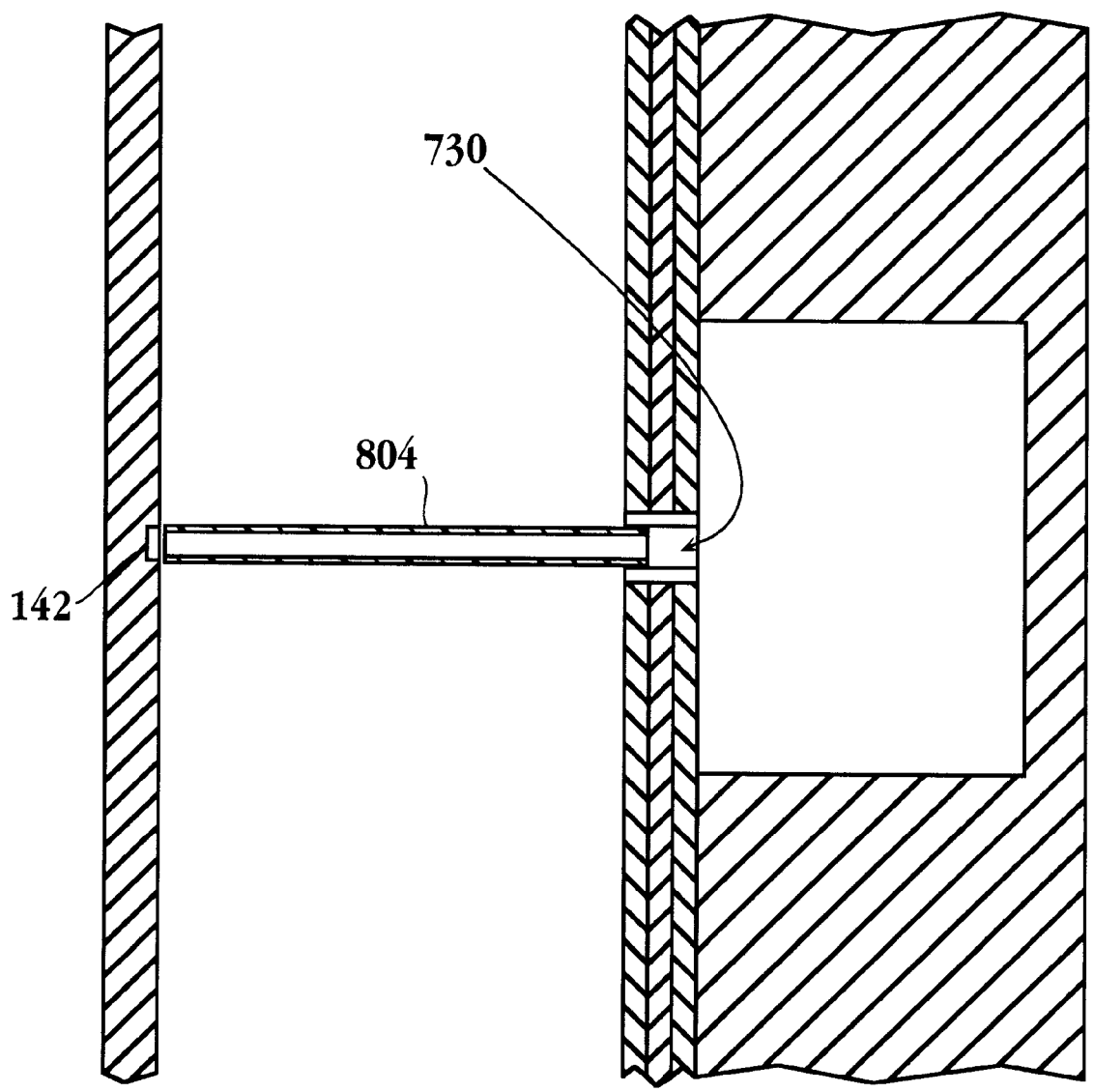
FIG. 19 is a cross-sectional view of an embodiment of the invention that includes a capillary.
Figure 20:
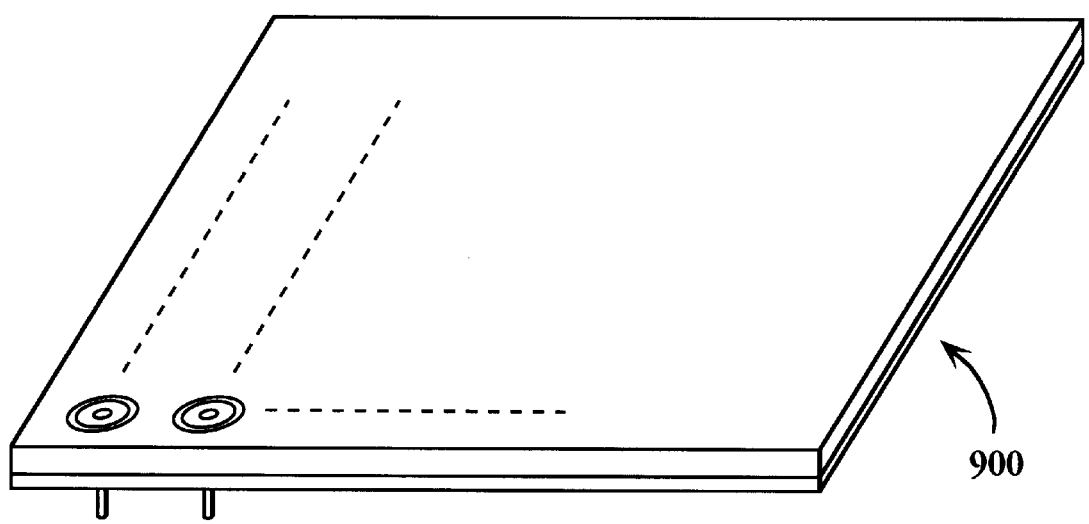
FIG. 20 is a perspective view of an embodiment of the invention that includes an array of capillaries.

VIII. In another embodiment, as shown in FIG. 19, the present invention may be employed in conjunction with capillary size dispensing tubes 804 associated with the apertures 703 of the present devices. The capillary tubes are used to form small drops of fluid and locate them precisely on substrate surfaces 142 in miniature arrays. The printed arrays may consist of nucleic acids, peptides, immunoassay reagents, pharmaceutical test compounds and the like. As shown in FIG. 20, the array 900 of capillary dispensing tubes in fluid communication with the array of source wells may be used to locate the drops on a substrate in predetermined patterns. Nanoliter quantities of liquids may be dispensed. Arrays of biological samples as dense as approximately sixteen hundred per square centimeter with center to center spacing as small as about two hundred fifty micrometers may be formed.

The length and the bore diameter of the dispensing capillary control the volume of liquid drawn into the dispensing capillary. Those skilled in the art will recognize a large number of capillaries useful for practicing this invention. For example, fused silica may be used with an outside coating of polyimide for strengthening with inside bore ID's from about 10 to 200 microns, more typically from about 25 to 100 microns and OD's greater than about 200 microns. Typically, the length of the dispensing capillary could range up to about 10 to 20 mm. Dispensing capillaries of these dimensions can fill with sample volumes in the 1 to 10 microliter range. The volume of liquid drawn into the dispensing capillary can be controlled by defining the bore diameter and the length of the dispensing capillary. The latter dimension can be defined by positioning a stop junction along the inner wall of the dispensing capillary. This stop junction could be an abrupt increase in the bore diameter of the dispensing capillary. Alternatively, surface treatment procedures may be used for controlling the amount of liquid the dispensing capillary can hold.

In a preferred embodiment, the dimensions of the capillaries are about 0.001 to 0.020 inches in diameter, preferably 0.005 to 0.01 inches in diameter, preferably, about 100 micrometers inner diameter and about 250 micrometers outer diameter. The dimensions of the resulting spots are about 125 micrometers diameter with a center to center spacing of 250 micrometers. The resulting array has a density of about 1600 per square centimers.

In another approach an electrically conducting collar is deposited to a capillary. One end of the capillary is attached to the device of the invention through a liquid filled line and the other end of the capillary is for dispensing. When a voltage is applied to the collar, it electrostatically sprays a defined volume of liquid. The volume of the drop is dependent upon a number of factors that include the diameter of the capillary, the viscosity of the liquid, the intensity and the duration of the voltage pulse and so forth. A single voltage pulse produces a drop of approximately 200 picoliters. With a frequency of about 1000 pulses per second, a volume of about 0.2 microliters per second will be delivered.

A particular device in accordance with the above embodiment has a sample handling plate with an array of sample handling wells, which contain liquid samples, with a corresponding array of capillaries extending from the aperture of the sample handling plate. When the dispensing capillaries are in the sample, an aliquot of sample is transferred to the dispensing capillary by combination of electrostatic and capillary action. The device comprises a plate having an array of transfer elements, each of which comprises an aperture in the plate with a protrusion depending therefrom. In this embodiment the protrusion is formed in the plate, which is permanently, non-removably attached to the plate. The plate is manufactured from an electroconductive material and is usually about 0.1 to about 10 mm in thickness, preferably about 1 to about 5 mm in thickness. In a particular embodiment the plate is a thin metal foil secured to the plate and perforated in a precision manner to produce the protrusions with openings. Each opening contains a hollow capillary tube with a channel. The dimensions of the channel will depend on the dimensions of the transfer elements or of a microfluidic system.

As mentioned above, in the present invention an array of samples in a multiwell source plate are simultaneously transferred to an array of microassay reservoirs of plate comprising an array of microfluidic networks by means of a device having a plurality of transfer elements. The microfluidic network plate contains 96, 384, or 1536 receiving reservoirs or sites on its bottom surface. These reservoirs are connected to mixing, reaction, and separation channels in the microfluidic network plate. The present device contains an active liquid transfer means over each well of a multiwell plate such as a source or library plate, to which the present device is attached. Upon activation, the transfer elements in the present device move an amount of liquid from the wells of the library plate to the microfluidic network plate, in which the sample processing and analysis take place. The present devices are attached to the library plate after the source plate is created and stays attached during normal use. In the present invention there is no element that is immersed in the sample to be processed. The present device alleviates debris contamination and prevents evaporation of the liquid in the wells.

Once the samples have been transferred in accordance with the present invention to a microfluidic network, the samples may be processed. A sample may be processed by one or more of any number of procedures such as, for example, separating or classifying compounds, replicating or amplifying components, degrading components, polymerizing components, and other similar modifications, and so forth. Examples of such procedures include subjecting such sample to separation procedures for sample enrichment, isolation or purification, analyzing such sample such, e.g., as an assay, detection and the like, carrying out a chemical synthesis with such sample, such as those involved with combinatorial chemistry methods for small and large molecule synthesis, screening for therapeutic drugs, receptor-ligand binding analysis, screening for agonist/antagonist behavior of compounds, DNA and protein sequencing, genotyping, oligosaccharide profiling, and so forth. For example, polynucleotides may be synthesized or sequenced. Different nucleotides can be reacted to form DNA and different amino acids can be reacted to form proteins. These reactions can be carried out at greatly increased speeds as compared with conventional mechanical technologies. In addition to increased speeds, the yield is vastly improved due to the precision with which the reactants can be moved in accordance with the present invention.

Reactions may include catalytic and affinity reactions. Although enzymes are the typical biocatalyst employed for bioanalytical applications, catalytic antibodies and catalytic RNA are also to be included, among others. Affinity-based reactions may include, but are not limited to, receptor-mediated ligand binding, DNA or RNA hybridization, and immuno-reactions. The later is not limited to antibody-antigen interactions and can include antibody-hapten, antibody-nucleic acid binding, antibody-antibody interactions, and antibody-receptor binding.

In addition to the separation, synthesis and sequencing methods described above, the present invention is useful for a variety of additional purposes. For example, it is possible to utilize specific embodiments of the invention in order to separate impurities from large mixtures of compounds and thus carry out a purification processing which is substantially more refined than vacuum fractionation processing. A mixture of components can be separated into a variety of pure groups and moved along parallel tracks. Upon resolving the mixtures, the desired components can be guided by the electrical fields to appropriate locations within one or more channels. Alternatively, selected components may be guided to channels filled with members of binding pairs, such as antigen-antibody pairs, reactive with given substances of interest. These substances of interest may be moving in the medium or be moved into contact with complementary components having a label, other member of a signal producing system, or other type of chemical for various transformations that are either physical or chemical in nature. Furthermore, bacterial or mammalian cells, or viruses may be sorted by complicated microfluidic networks in connection with a plurality of electrodes capable of generating electrical potentials of a variety of different strengths in order to move the cells, organelles, liposomes, and the like, or viruses, through the fields based on the size, charge or shape of the particular material being moved. Separated cells or viruses may be analyzed or modified subsequently, for example, by disruption to analyze or otherwise characterize its internal components.

The processing is generally carried out on a microfluidic scale with channel dimensions similar to those used typically in capillary electrophoresis. However, there may be regions with larger than capillary-scale dimensions for purposes of increasing surface area reaction volume, accommodating highly dilute sample or interfacing with existing equipment. The miniaturized system of enrichment trenches, reaction chambers and detection zones enable multiple laboratory processes to be integrated "on-board" a planar substrate, including sample preparation, incubation, electrophoretic separations, and analyses.

The sample is usually a medium containing a substance of interest, synthetic or natural, to be examined, treated, determined or otherwise processed. Typical sources for mammalian biological samples include body fluids such as, for example, whole blood, blood fractions such as serum and plasma, synovial fluid, cerebro-spinal fluid, amniotic fluid, semen, cervical mucus, sputum, saliva, gingival fluid, urine, and the like. Other sources include culture samples, bioprocessing fluids, food and beverage water, air and soil samples, and so forth. In addition, sample includes combinatorial chemistry generated libraries of compounds, usually small molecules, oligonucleotides and peptides. Other sources of samples are aqueous or water soluble solutions of natural or synthetic compounds, particularly, compounds that are potential therapeutic drugs where it is desired to determine if the compound binds to a specific receptor.

The amount of the sample depends on the nature of the sample and the nature of the processing to be conducted. For fluid samples such as whole blood, saliva, urine and the like the amount of the sample is usually about 1 to 1000 nanoliters, more usually, about 10 to 100 nanoliters. The sample can be pretreated and can be prepared in any convenient medium, which does not interfere with a microfluidic process in accordance with the present invention. An aqueous medium is preferred.

The substance can be comprised of a member of a specific binding pair (sbp) and may be a ligand, which is monovalent (monoepitopic) or polyvalent (polyepitopic), synthetic or natural, antigenic or haptenic, and is a single compound or plurality of compounds which share at least one common epitopic or determinant site. The substance of interest can be a part of a cell such as bacteria or a cell bearing a blood group antigen such as A, B, D, etc., or an HLA antigen, or cell membrane receptors, or a microorganism, e.g., bacterium, fungus, protozoan, or virus.

The monoepitopic ligands will generally be from about 100 to 2,000 molecular weight, more usually from 125 to 1,000 molecular weight. The substances of interest include drugs, potential drug candidates, metabolites, pesticides, pollutants, and the like. The polyvalent ligands will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligands to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

For receptors, the molecular weights will generally range from 10,000 to 2×108, more usually from 10,000 to 106. For immunoglobulins, IgA, IgG, IgE and IgM, the molecular weights will generally vary from about 160,000 to about 106. Enzymes will normally range from about 10,000 to 1,000,000 in molecular weight. Natural receptors vary widely, generally being at least about 25,000 molecular weight and may be 106 or higher molecular weight, including such materials as avidin, DNA, RNA, thyroxine binding globulin, thyroxine binding prealbumin, transcortin, etc.

Also included are polynucleotides such as m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

A member of a specific binding pair ("sbp" member) is generally one of two different molecules having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. Complementary sbp members bind to one another, as for example, a ligand and its complementary receptor. With respect to two complementary sbp members, one may be referred to as the "binding partner" for the other. Sbp members can be immunological pairs such as antigen and antibody, or non-immunological pairs such as avidin and biotin. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin B12, with the corresponding receptors being avidin or streptavidin, anti-lysergic acid, anti-fluorescein and intrinsic factor, respectively.

The ligand is any organic compound for which a receptor naturally exists or can be prepared. Receptors ("antiligand") are any compound or composition capable of recognizing a particular spatial and polar organization of a molecule, e.g., epitopic or determinant site. Illustrative receptors include membrane bound receptors such as G-protein receptors (e.g., muscarinic, adrenergic, prostaglandin and dopamine such as the D2 receptor), tyrosine kinase (insulin-like IGF, epidermal EGF, nerve NGF, fibroblast FGF growth factors), ion channels, T-cell receptors, the interleukins, and other naturally occurring receptors, e.g., thyroxine binding globulin, antibodies, enzymes, Fab fragments, lectins, nucleic acids, protein A, complement component C1q, and the like.

In an assay and in screening methods it is often desirable to use a label or reporter molecule, which is a chemical entity capable of being detected by a suitable detection means, including, but not limited to, spectrophotometric, chemiluminescent, electrochemical or radiochemical means. The reporter molecule can be conjugated to another molecule such as an sbp member, e.g., a ligand or an antibody, by procedures well known in the art. Typically, the reporter molecule contains a functional group suitable for attachment to the sbp member. The functional groups suitable for attaching the reporter group are usually activated esters or alkylating agents. Details of techniques for attaching reporter groups are well known in the art. See, for example, Matthews, et al., *Anal. Biochem.* (1985) 15:205–209 and Engelhardt, et al., European Patent Application No. 0302175.

Reporter molecules are members of a signal producing system capable of being detected directly or through a specific binding reaction to produce a detectable signal. The reporter molecule can be isotopic or nonisotopic, usually nonisotopic, and can be a catalyst, dye, fluorescent molecule, chemiluminescent molecule, coenzyme, enzyme, substrate, radioactive group, certain particles such as carbon and the like.

The labels or reporter molecules are usually part of a signal producing system ("sps"). The label and optionally other sps members are bound to an sbp member. Preferably, the label is an enzyme, electroluminescent group such as a transition metal complex (see, e.g., U.S. Pat. Nos. 5,541,113, 5,610,017, 5,527,710, 5,591,581, the relevant disclosures of which are incorporated herein by reference, chemiluminescer, fluorescer, radiolabel, or the like. Thus, with the above labels the signal is preferably detected and/or measured by detecting enzyme activity, luminescence, or light emissions, respectively. The labels and other reagents of the signal producing system must be stable at the temperatures used in the electroseparation method and subsequent assay.

Suitable labels include, by way of illustration and not limitation, enzymes such as alkaline phosphatase, glucose-6-phosphate dehydrogenase ("G6PDH") and horseradish peroxidase; promoters; dyes; fluorescers, such as fluorescein, isothiocyanate, rhodamine compounds, phycoerythrin, phycocyanin, allophycocyanin, o-phthaldehyde, and fluorescamine; electroluminescent labels such as ruthenium chelates; chemiluminescers such as isoluminol; sensitizers; coenzymes; enzyme substrates; radiolabels such as 125I, 131I, 14C, 3H, 57Co and 75Se. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

Some labels can directly produce a signal, and therefore, additional components are not required to produce a signal. Numerous organic molecules, for example fluorescers, are able to absorb ultraviolet and visible light, where the light absorption excites these molecules to an excited energy state. This absorbed energy is then dissipated by emission of light at a second wavelength. Other labels that directly produce a signal include radioactive isotopes and dyes.

Alternately, the label may need other components to produce a signal. In this situation the signal producing system would then include all the components required to produce a measurable signal. These components may include substrates, electron transfer agents, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, columns 11–13, incorporated herein by reference.

The label can be bound covalently to numerous sbp members: an antibody; a receptor for an antibody; a receptor that is capable of binding to a small molecule conjugated to an antibody, a ligand analog, an oligonucleotide and the like. Bonding of the label to the sbp member may be accomplished by chemical reactions that result in replacing a hydrogen atom of the label with a bond to the sbp member or may include a linking group between the label and the sbp member. Other sps members may also be bound covalently to sbp members such as avidin-biotin, fluorescein-antifluorescein, and the like. Two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See for example, Rubenstein, et al., and U.S. Pat. No. 3,817,837, incorporated herein by reference. Alternatively, one label may be bound to the particles of this invention and a second label bound to a sbp member that binds to the sbp member attached to the particle.

As mentioned above, the microfluidic processing includes assays. Generally, an assay is a method for determining a substance capable of binding to a specific binding pair member, for example, for determining an analyte or detecting the degree of binding of a compound to a receptor. The determination may be qualitative or quantitative. Such assays depend on specific binding of a ligand to its receptor and include receptor binding assays, immunoassays, ligand/binding assays, polynucleotide assays, particularly polynucleotide hybridization assays, and cell surface binding assays. The assays may be utilized for drug discovery and screening, studies of receptors, detection of drugs and other substances, DNA detection, DNA sequencing, genetic analysis, monitoring of gene expression, and so forth. One particular assay is the immunoassay, which is a specific binding assay in which the reagents include an antibody.

Antibodies are immunoglobulins that specifically bind to, and are thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular molecule is maintained.

The assays may be heterogeneous or homogeneous. A heterogeneous assay is an assay wherein free labeled species is separated from a labeled species that is bound to another species such as an sbp member. The separation may be carried out by physical separation, e.g., by transferring one of the species to another reaction vessel, filtration, centrifugation, chromatography, solid phase capture, magnetic separation, and so forth and may include one or more washing steps. The separation may be nonphysical in that no transfer of one or both of the species is conducted, but the species are separated from one another in situ. In the heterogeneous assay the activity of a label is not affected by the reaction of specific binding pair members with one another. Regardless of the means of separation, the signal from the label may be measured from one or both of the separated species.

A homogeneous assay is an assay wherein free labeled species is not separated from a labeled species that is bound to another species such as an sbp member. The signal from the label is significantly different between the free labeled species and that which is bound and, thus, can be measured without separation.

Another aspect of the present invention comprises kits for processing a sample. In one embodiment a kit comprises a device or an apparatus as described above and reagents, other than reagents within the apparatus, for processing a sample. The kit may also include one or more microfluidic network plates. The reagents for the kits may be packaged in the same or separate containers, so that the concentration of the reagents provides for substantial optimization of the method and assay. The reagents may each be in separate containers or various reagents can be combined in one or more containers depending on the cross-reactivity and stability of the reagents. Under appropriate circumstances one or more of the reagents in the kit can be provided as a dry powder, usually lyophilized, including excipients, which on dissolution will provide for a reagent solution having the appropriate concentration for performing a method or assay in accordance with the present invention. The kit can also include additional reagents depending on the nature of the method for which the kit is used. For example, the kit may include solid phase extraction materials including paramagnetic beads and non-magnetic particles, lysis solutions, wash and elution and running buffers, biomolecular recognition elements including receptors, enzymes, antibodies and other specific binding pair members, labelling solutions, substrates, reporter molecules, sample purification materials including membranes, beads, and the like, and so forth.

What is claimed is:

1. A device comprising:
    (a) a first plate having a plurality of transfer elements, each transfer element comprising an aperture in said plate wherein said aperture is capable of being electrically activated;
    (b) a multiwell plate comprising a plurality of wells;
    (c) one or more attaching elements on a first side of said first plate for sealingly attaching said first plate to said multiwell plate to form a sealed system except for said apertures;
    (d) electrodes for electrically activating said aperture.

2. The device of claim 1 wherein each of said transfer elements further comprises a nozzle on a second side of said plate as an extension of said aperture wherein said nozzle is formed from an electroconductive material.

3. The device of claim 2 wherein said electroconductive material is adapted for activation by an applied electric potential.

4. The device of claim 1 wherein said attaching element is removably attachable to said multiwell plate.

5. An apparatus for transferring liquid, said apparatus comprising:
    (a) a first plate comprising a plurality of individual wells containing said liquid, said wells being formed in said first plate on a first side thereof, wherein a second side of said first plate is free of openings;
    (b) a second plate comprising a first side and a second side and a plurality of transfer elements, each transfer element comprising an aperture in said second plate, wherein said apertures are capable of being electrically activated, said second plate being adapted for simultaneously transferring precise amounts of a liquid from said first plate to a sample receiving plate by electrically activating said apertures, said second side of said second plate being sealingly attached to the first side of said first plate; and
    (c) electrodes for electrically activating said aperture.

6. The apparatus of claim 5, further comprising a sample receiving plate, wherein said sample receiving plate comprises a plurality of sample receiving reservoirs that are part of a microfluidic network.

7. The apparatus of claim 6 wherein said apertures are comprised of an electroconductive material serving as a first electrode and said sample receiving plate has a second electrode adjacent thereto and cooperative with said first electrode to provide for application of an electric potential between said electroconductive material and said second electrode.

8. The apparatus of claim 5 wherein each of said transfer elements further comprises a nozzle on a second side of said plate as an extension of said aperture wherein said nozzle is formed from an electroconductive material.

9. The apparatus of claim 5 wherein said second side of said second plate comprises one or more friction members to render said second plate sealingly attached to the first side of said first plate.

10. The apparatus of claim 9 wherein said second plate is removably attached to the first side of said first plate.

11. The apparatus of claim 5 wherein said second side of said second plate comprises an adhesive layer to render said second plate sealingly attached to the first side of said first plate.

12. The apparatus of claim 5 which further comprises an acceleration electrode.

13. The apparatus of claim 5 which further comprises an array of capillaries.

14. A method for trnsfering liquid, said method comprising:
    (a) disposing a quantity of liquid to a second side of a plate having a plurality of apertures therein that are capable of being electrically activated, wherein said liquid is present in a closed container comprising individual wells of a multiwell plate and
    (b) electrically activating said apertures.

15. The method of claim 14 wherein said container is a well that is part of a 96 multiwell plate.

16. The method of claim 15 wherein said well of said multiwell plate comprises a bottom wall wherein said bottom wall is substantially free of contact with said liquid.

17. The method of claim 15 wherein said second side of said plate comprises one or more friction members to render said plate sealingly attached to said multiwell plate to form said closed system.

18. The method of claim 17 wherein said multiwell plate is removably attached to the first side of said first plate.

19. The method of claim 14 wherein said apertures are part of transfer elements, each of said transfer elements comprising a nozzle on a first side of said plate as an extension of said aperture wherein said nozzle is formed from an electroconductive material.

20. The method of claim 14 wherein said second side of said plate comprises an adhesive layer to render said plate sealingly attached to said multiwell plate to form said closed system.

21. A method for transferring liquid, said method comprising:
    (a) providing a first plate comprising a plurality of individual wells containing said liquid, said wells being formed in said first plate on a first side thereof,
    (b) providing a second plate comprising a first side and a second side and a plurality of transfer elements, each transfer element comprising an aperture in said second plate, wherein said apertures are capable of being electrically activated, said second plate being adapted for simultaneously transferring precise amounts of a liquid from said first plate to a sample receiving plate by electrically activating said apertures,
    (c) sealingly attaching said second side of said second plate to the first side of said first plate,
    (d) positioning said apertures adjacent to an array of sample receiving plate, and
    (e) electrically activating said apertures.

22. The method of claim 21 wherein said sample receiving plate comprises a plurality of sample receiving reservoirs that are part of a microfluidic network.

23. The method of claim 21 wherein said apertures are comprised of an electroconductive material serving as a first electrode and said sample receiving plate has a second electrode adjacent thereto and cooperative with said first electrode to provide for application of an electric potential to electrically activate said apertures.

24. The method of claim 21 wherein each of said transfer elements further comprises a nozzle on a first side of said plate as an extension of said aperture wherein said nozzle is formed from an electroconductive material.

25. The method of claim 21 wherein said second side of said second plate comprises one or more friction members to render said second plate sealingly attached to the first side of said first plate.

26. The method of claim 25 wherein said second plate is removably attached to the first side of said first plate.

27. The method of claim 21 wherein said second side of said second plate comprises an adhesive layer to render said second plate sealingly attached to the first side of said first plate.

28. A method for transferring liquid, said method comprising:
(a) attaching, to a multiwell plate having liquid contained in the wells thereof, a second plate comprising a first side and a second side and a plurality of apertures therethrough, each of said apertures being at least partially comprised of an electroconductive material, each of said apertures being aligned with a corresponding well of said multiwell plate, said second plate comprising on said second side one or more attaching elements and said second plate being attached to the top of said multiwell plate by said attaching element,
(b) inverting said multiwell plate attached to said second plate so that liquid is disposed at each of said apertures, the dimensions of said apertures being such that liquid does not exit said apertures,
(c) positioning said apertures adjacent to an array of sample receiving reservoirs of a microfluidic network in a third plate wherein each of said microfluidic networks has an electrode connected to an electrode adjacent one of said apertures,
(d) applying an electric potential across said electrodes causing a portion of said liquid to exit said apertures and enter a corresponding sample receiving reservoir.

29. The method of claim 28 wherein said apertures are part of a transfer element, each of said transfer elements further comprising a nozzle on a first side of said plate as an extension of said aperture wherein said nozzle is formed from an electroconductive material.

30. The method of claim 28 wherein said attaching element comprises one or more friction members.

31. The method of claim 28 wherein said attaching element comprises an adhesive layer.

32. A kit comprising in packaged combination:
(a) the device of claim 1 and
(b) a sample receiving plate.

33. The kit of claim 32 wherein said sample receiving plate is selected from the group consisting of planar surfaces and sample receiving reservoirs.

34. The kit of claim 32 which comprises one or more reagents for conducting a chemical synthesis or an analysis.

35. The kit of claim 32 which comprises a multiwell plate.

* * * * *